US007315864B2

(12) United States Patent
Valentine

(10) Patent No.: US 7,315,864 B2
(45) Date of Patent: Jan. 1, 2008

(54) SYSTEM AND METHOD FOR CREATING A BOOK OF REPORTS OVER A COMPUTER NETWORK

(76) Inventor: Edmund L. Valentine, 10 Farm Hill Rd., Stamford, CT (US) 06902

( * ) Notice: Subject to any disclaimer, the term of this patent is extended or adjusted under 35 U.S.C. 154(b) by 0 days.

(21) Appl. No.: 09/798,460

(22) Filed: Mar. 2, 2001

(65) Prior Publication Data

US 2001/0037334 A1 Nov. 1, 2001

Related U.S. Application Data

(60) Provisional application No. 60/186,851, filed on Mar. 2, 2000.

(51) Int. Cl.
*G06F 17/00* (2006.01)
(52) U.S. Cl. .................. 707/102; 707/101; 707/103 X; 707/104.1
(58) Field of Classification Search ............... 707/102, 707/1, 2, 3, 101, 103 R, 104.1; 709/203; 705/26
See application file for complete search history.

(56) References Cited

U.S. PATENT DOCUMENTS

| 4,975,840 | A | | 12/1990 | DeTore et al. | |
|---|---|---|---|---|---|
| 5,008,853 | A | | 4/1991 | Bly et al. ................... | 715/751 |
| 5,061,916 | A | * | 10/1991 | French et al. ............... | 340/522 |
| 5,517,405 | A | | 5/1996 | McAndrew et al. | |
| 5,537,590 | A | * | 7/1996 | Amado .......................... | 707/2 |
| 5,555,098 | A | * | 9/1996 | Parulski ...................... | 386/104 |
| 5,634,051 | A | | 5/1997 | Thomson | |
| 5,694,594 | A | | 12/1997 | Chang | |
| 5,715,443 | A | | 2/1998 | Yanagihara et al. | |
| 5,729,674 | A | | 3/1998 | Rosewarne et al. ......... | 345/634 |
| 5,732,397 | A | | 3/1998 | DeTore et al. | |
| 5,784,635 | A | | 7/1998 | McCallum | |
| 5,819,273 | A | | 10/1998 | Vora et al. | |
| 5,878,421 | A | * | 3/1999 | Ferrel et al. ................. | 707/100 |
| 5,883,635 | A | * | 3/1999 | Rao et al. .................... | 345/440 |
| 5,893,109 | A | * | 4/1999 | DeRose et al. .......... | 707/104.1 |
| 5,907,836 | A | | 5/1999 | Sumita et al. .................. | 707/2 |
| 5,915,240 | A | | 6/1999 | Karpf | |
| 5,924,090 | A | | 7/1999 | Krellenstein | |
| 5,956,708 | A | | 9/1999 | Dyko et al. ..................... | 707/3 |
| 5,978,804 | A | | 11/1999 | Dietzman | |
| 5,978,818 | A | * | 11/1999 | Lin .......................... | 715/501.1 |
| 5,987,454 | A | | 11/1999 | Hobbs | |
| 5,987,457 | A | | 11/1999 | Ballard | |

(Continued)

OTHER PUBLICATIONS http://www.bizcharts.com/Software for Business Intelligence, Biznet Solutions, Updated Jan. 2000; printed on Jan. 20, 2000.

(Continued)

*Primary Examiner*—Thuy Pardo
(74) *Attorney, Agent, or Firm*—McCarter & English, LLP

(57) ABSTRACT

A method is disclosed wherein a server receives and stores report definitions. A user instructs the server to create a book and associate the report definitions with the book. Thereafter, the user requests that the server generate and transmit the book to his client. The server generates and transmits a report for each of the report definitions to the user.

53 Claims, 35 Drawing Sheets

U.S. PATENT DOCUMENTS

| | | | |
|---|---|---|---|
| 5,987,482 A * | 11/1999 | Bates et al. | 715/513 |
| 5,991,758 A | 11/1999 | Ellard | |
| 6,055,544 A * | 4/2000 | DeRose et al. | 707/104.1 |
| 6,195,093 B1 * | 2/2001 | Nelson et al. | 345/732 |
| 6,212,527 B1 * | 4/2001 | Gustman | 707/102 |
| 6,233,583 B1 * | 5/2001 | Hoth | 707/102 |
| 6,240,412 B1 * | 5/2001 | Dyko et al. | 707/5 |
| 6,281,986 B1 * | 8/2001 | Form | 358/403 |
| 6,369,835 B1 * | 4/2002 | Lin | 345/726 |
| 6,377,956 B1 * | 4/2002 | Hsu et al. | 707/104.1 |
| 6,662,179 B2 * | 12/2003 | Benjamin et al. | 707/3 |
| 6,871,112 B1 * | 3/2005 | Coss et al. | 700/121 |
| 6,874,010 B1 * | 3/2005 | Sargent | 709/203 |
| 2002/0184059 A1 * | 12/2002 | Offutt et al. | 705/5 |
| 2002/0198957 A1 * | 12/2002 | Amjadi | 709/217 |
| 2003/0065591 A1 * | 4/2003 | Jones | 705/28 |

OTHER PUBLICATIONS http://www.bizcharts.com/scpharm/21chart.htm/BizInt Smart Charts for Pharmaceuticals Version 2.1—Sample Chart, 1999; printed on Jan. 20, 2000.

http://www.bizcharts.com/scpharm/21 spec.htm/BizInt Smart Charts for Pharmaceuticals 2.1—Specifications; printed on Jan. 20, 2000.

http://www.bizcharts.com/scpharm/index.html/BizInt Smart Charts for Pharmaceuticals Version 2.1; printed Jan. 20, 2000.

BizInt Smart Charts for Pharmaceuticals Version 2.1—Quick Guide; printed Jan. 20, 2000.

http://www.bizcharts.com/sc4pats/index.html/BizInt Smart Charts for Patents Version 1.1; printed Jan. 25, 2000.

http://www.bizcharats.com/pressrel.htm/BizInt Solutions—Press Release Nov. 27, 1996; printed on Jan. 20, 2000.

BizInt Smart Charts, IMS R&D Focus.

BizInt Smart Charts, PJB Pharma projects (Qty 2 charts).

BizInt Smart Charts, IMS R&D Focus (Qty 9 charts).

Antisense oligonucleotide, ICAM-1 (antisense oligonucleotide, intracellular adhesion molecule-1, ISIS 2302) IMS R&D Focus; Publication Date: Oct. 19, 1988.

Apafant (WEB 2086, web 2086BS), IMS R&D Focus; Dec. 1, 1997.

* cited by examiner

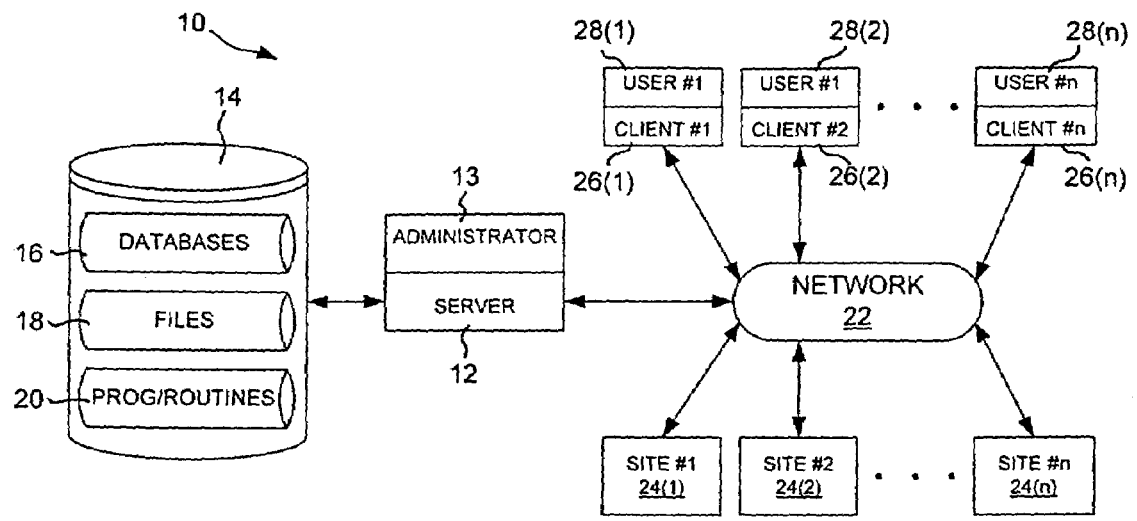
FIG. 1
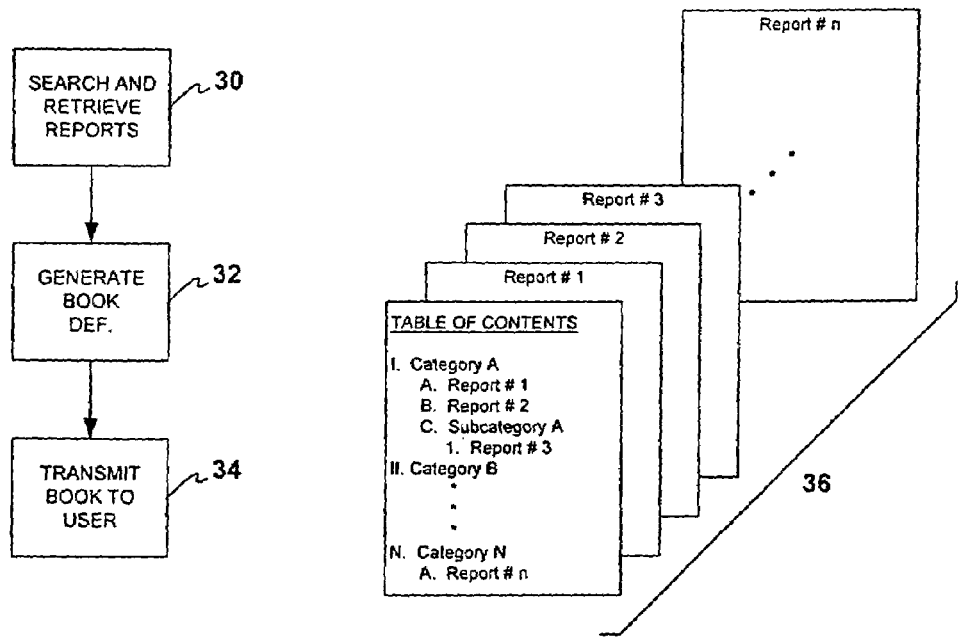
FIG. 2
FIG. 3A

[BOOK TITLE]
Generation Date: 1/1/00 9:00 am

TABLE OF CONTENTS

ANGIOGENESIS MECHANISMS OF ACTION REPORT ................................................. 1
    U.S. PRODUCTS IN DEVELOPMENT

IRTEMAS -- PRODUCT REPORT .................................................................................. 2

DATABASE DETAIL FOR: IRTEMAS ............................................................................ 2
    R&D FOCUS DETAIL FOR: IRTEMAS ........................................................................... 3
    PHARMAPROJECTS DETAIL FOR: IRTEMAS ............................................................ 5

ER-90 -- PRODUCT REPORT ........................................................................................ 7

DATABASE DETAIL FOR: ER-90 ................................................................................. 7
    R&D FOCUS DETAIL FOR: URATE OXIDASE (SYNONYM) ..................................... 8
    PHARMAPROJECTS DETAIL FOR: ER-90 ................................................................ 10

TM-87 -- PRODUCT REPORT ..................................................................................... 12

DATABASE DETAIL FOR: TM-87 .............................................................................. 12
    R&D FOCUS DETAIL FOR: TELE-201 (SYNONYM) ................................................. 14
    PHARMAPROJECTS DETAIL FOR: TM-87 ............................................................... 16

FIG 3B

ANGIOGENESIS MECHANSIMS OF ACTION REPORT U.S.
PRODUCTS IN DEVELOPMENT
(Those available for licensing are indicated by a "Y")

| Brand ID | Parent Company | Subsidiary Company | Licensors | Brand Name | Generic/ Synonym Names | Mechanisms of Action | Diagnoses | WW Lifecycle | US Lifecycle | WW Lic Opp | US Lic Opp | Angiogenesis Inhibitor | Angiogenesis Stimulant |
|---|---|---|---|---|---|---|---|---|---|---|---|---|---|
| 253 | ABE | ABE Laboratory | Hartwick University | AMG 130 | AMG 130; TP 26 | Angiogenesis inhibitor; antibiotic | Breast Cancer; Cancer; Cervical Cancer; Prostate Cancer, Renal Cancer | | | | | II | |
| 380 | Eternal | Eternal Pharma | Eternal Pharma | Neoval | Neoval; AR94; POVOCAL | Angiogenesis stimulant; NSAID | Acne; Acne Rosacea; Breast Cancer; Cancer; Colon Rectal Cancer; Eye Disease; Lung Cancer | | | | | | III |
| 24 | Argon | Argon Pharmaceuticals | Argon Pharmaceuticals | GA 343 | GA 343; Tesprenese | Angiogenesis inhibitor;matrix metalloproteinase inhibitor; Metalloproteinase inhibitor | Cancer. Colon Rectal Cancer; Kidney Cancer; Lung Cancer, Advanced; Lung Cancer, Non-Small Cell; Malanoma | III | III III | Y | Y | | |
| 225 | Zen-Astra | Zen-Astra | Carbonod | CC-112 | CC-112; Carbonod; BGS toxin | Angiogenesis inhibitor; Complement factor stimulant; Immunostimulant; polysacharide | Cancer; Spinal Cord Injury; Tumors | II | II | | | II | |

FIG. 3C

Diagnosis Filters

Remove Selected | Cancel

Diagnosis Groups Selected | Add
(none selected)

Diagnosis SubGroups Selected | Add
(none selected)

Individual Diagnosis Selected | Add
(none selected)

250

Select Individual Diagnosis
Enter Search text: Diabetes | Find
255
Please enter Search text above
then press "Find" to List Diagnosis Select Individual Diagnosis
Enter Search text: Diabetes | Find
Apply | Cancel
256
6 matching diagnosis found
☐ Diabetes
☐ Diabetes Insipidus
☐ Diabetes Mellitus
☐ Diabetes general (Diabetes)*
☐ Diabetes, type I (Type 1 Diabetes Mellitus)*
☐ Diabetes, type II (Type 2 Diabetes Mellitus)*
*Corrected Diagnoses shown in Parentheses

FIG. 8C

Select Therapeutic Groups [Apply] [Cancel]

251

☐ CARDIOVASCULAR SYSTEM DISORDERS
☐ CLINICAL PHARMACOLOGY
☐ DENTAL AND ORAL DISORDERS
☐ DERMATOLOGICAL DISORDERS
☐ DIAGNOSTIC AIDS
☐ EAR, NOSE, MOUTH AND THROAT DISORDERS
☐ ENDOCRINE DISORDERS
☐ GASTROINTESTINAL SYSTEM DISORDERS
☐ GYNECOLGIC AND OBSTRETIC DISORDERS
☐ HEMATOLOGIC DISORDERS
☐ HEPATOBILUARY SYSTEMS DISORDERS
☐ IMAGING AGENTS
☐ IMMUNOLOGY AND ALLERGIC DISORDERS
☐ INFECTIOUS DISEASES
☐ MUSCULOSSKELETAL & CONNECTIVE TISSUE DISORDERS
☐ NEUROLOGICAL DISORDERS
☐ NUTRITIONAL AND METABOLIC DISORDERS
☐ ONCOLOGIC DISORDERS
☐ OPTHAMLOLOGIC DISORDERS
☐ OTHERS
☐ Pain, Analgesics & Anesthesia
☐ PEDIATRIC AND GENETIC DISORDERS
☐ PROCEDURES
☐ PSYCHIATRIC DISORDERS
☐ RENAL AND GENITOURINARY DISORDERS
☐ REPRODUCTIVE
☐ RESIRATORY SYSTEM DISORDERS
☐ Technologies (Reclassification By MMC is Not Finis
☐ Transplant
☐ UNCLASSIFIED Select Diagnosis SubGroups    252    [Apply] [Cancel]
Diagnosis Groups [ENDOCRINE DISORDERS ▽]    [Refresh]

253

ENDOCRINE DISORDERS
GASTROINTESTINAL SYSTEM DISORDERS
GYNECOLGIC AND OBSTRETIC DISORDERS
HEMATOLOGIC DISORDERS
HEPATOBILUARY SYSTEMS DISORDERS
IMAGING AGENTS
IMMUNOLOGY AND ALLERGIC DISORDERS
INFECTIOUS DISEASES
MUSCULOSSKELETAL & CONNECTIVE TISSUE DISORDERS
NEUROLOGICAL DISORDERS
NUTRITIONAL AND METABOLIC DISORDERS

254

ENDOCRINE DISORDERS
☐ Diabetes
☐ Diabetes Complications
☐ Drugs
☐ Endocrine Disorders (General)
☐ Growth
☐ Hormones
☐ Thyroid

MechAction Filters

Remove Selected | Cancel

Therapeutic Groups Selected | Add
(none selected)

MechAction SubGroups Selected | Add
(none selected)

Individual Mechanisms of Action Selected | Add
(none selected)

260

Select Individual MechActions
Enter Search text: Angiogenesis | Find

265

Please enter Search text above,
then press "Find" to Mechanism of Action

Select Individual MechActions
Enter Search text: Angiogenesis | Find

Your profile allow you to select Mechanism of Action from 30 Therapeutic Groups 3 matching Mechanisms of Action found | Apply | Cancel 3 matching diagnosis found
☐ angiogenesis inducer
☐ Angiogenesis inhibitor
☐ angiogenesis stimulant

266

Select Therapeutic Groups [Apply] [Cancel]

- ☐ CARDIOVASCULAR SYSTEM DISORDERS
- ☐ CLINICAL PHARMACOLOGY
- ☐ DENTAL AND ORAL DISORDERS
- ☐ DERMATOLOGICAL DISORDERS  *261*
- ☐ DIAGNOSTIC AIDS
- ☐ EAR, NOSE, MOUTH AND THROAT DISORDERS
- ☐ ENDOCRINE DISORDERS
- ☐ GASTROINTESTINAL SYSTEM DISORDERS
- ☐ GYNECOLGIC AND OBSTRETIC DISORDERS
- ☐ HEMATOLOGIC DISORDERS
- ☐ HEPATOBILIUARY SYSTEMS DISORDERS
- ☐ IMAGING AGENTS
- ☐ IMMUNOLOGY AND ALLERGIC DISORDERS
- ☐ INFECTIOUS DISEASES
- ☐ MUSCULOSKELETAL & CONNECTIVE TISSUE DISORDERS
- ☐ NEUROLOGICAL DISORDERS
- ☐ NUTRITIONAL AND METABOLIC DISORDERS
- ☐ ONCOLOGIC DISORDERS
- ☐ OPTHAMLOLOGIC DISORDERS
- ☐ OTHERS
- ☐ Pain, Analgesics & Anesthesia
- ☐ PEDIATRIC AND GENETIC DISORDERS
- ☐ PROCEDURES
- ☐ PSYCHIATRIC DISORDERS
- ☐ RENAL AND GENITOURINARY DISORDERS
- ☐ REPRODUCTIVE
- ☐ RESIRATORY SYSTEM DISORDERS
- ☐ Technologies (Reclassification By MMC is Not Finis
- ☐ Transplant
- ☐ UNCLASSIFIED

Select Mechanism of Action SubGroups *262* [Apply] [Cancel]

Therapeutic Groups [ONCOLOGIC DISORDERS ▽] [Refresh]

```
ONCOLOGIC DISORDERS           △
OPTHAMLOLOGIC DISORDERS
OTHERS                    263
Pain, Analgesics & Anesthesia
PEDIATRIC AND GENETIC DISORDERS
PROCEDURES
PSYCHIATRIC DISORDERS
RENAL AND GENITOURINARY DISORDERS
REPRODUCTIVE
RESIRATORY SYSTEM DISORDERS
Technologies (Reclassification By MMC is Not Finished  ▽
```

Select Mechanism of Action SubGroups *262* [Apply] [Cancel]

Therapeutic Groups [ONCOLOGIC DISORDERS ▽] [Refresh]

ONCOLOGIC DISORDERS                                *264*
- ☐ Angiogenesis            ☐ Immunotherapy
- ☐ Apoptosis               ☐ Lipid Signaling
- ☐ Biotechnology           ☐ New Mechanisms
- ☐ Cell Cycle Therapies    ☐ Oncogene Signaling
- ☐ Cytotoxic               ☐ Protease Therapies
- ☐ Differentiation         ☐ Supportive Therapies
- ☐ G Protein Coupled Receptors  ☐ Uspecified 3
- ☐ Hematopostic Therapies
- ☐ Hormonal Therapies

FIG. 8F

| Title | Filters | Columns | Countries | Options |

Report Filters | Diagnosis | MechAction | Marketer | Life cycle | Status

270 — Lifycycle Filters

272 — Development | Marketed | Clear All | Cancel

☐ PT Prorected Non-Therapeutically Substituable
☐ PTP Protected But Therapeutically Substituable By Another Protected Agent
☐ PTP Protected But Therapeutically Substituable By Genegic Product
☐ PE Patent Expired No Competition
☐ PET Patent Expired, Therapeutically Substituable By A Protected Agent
☐ PET Patent Expired, Therapeutically Substituable By A Generic
☐ GLC Generic With Limited, Less Than Three, Competition
☐ G Generic
☐ M Marketed
☑ R Registered
☑ PR Pre-Registration
☑ III Phase III
☑ FT Fast Trac
☑ II Phase II
☑ I Phase I
☑ C Clinical Phase Unknown
☑ PC Preclinical
☐ W Withdrawn
☐ S Suspended
☐ D Discontinued
☑ TI Technology Investments
☑ U Unspecified
☐ AD Active Development
☐ ID Inactive Development

FIG. 8G

Click on Heading to set criteria:

370
- Diagnosis Groups: (no restriction specified)
- Diagnosis SubGroups: (no restriction specified)
- Individual Diagnoses: Gout ☐ Delete 372
- Parent Companies: (no restriction specified)
- Subsidiary Companies: (no restriction specified)

374
- Mechanisms of Action Therapeutic Groups: (no restriction specified)
- Mechanisms of Action: (no restriction specified)

376
- Lifesycles: III: Phase III ☐ Delete
- II: Phase II ☐ Delete
- Compound Status: AD: Development ☐ Delete
- ID: Inactive DEvelopment ☐ Delete 378
- Countries: (no restriction specified)

380 — Run Query  [Remove Marked Rows] [Mark All] [Mark None]

FIG. 10B

Product Query- Results:
Download this Report in RTF Format:

Selected Diagnosis Groups: (any)

Selected Diagnosis SubGroups: (any)

Selected Diagnosis: Gout

Selected Mechanism of Action Therapeutic Groups: (any)

Selected Mechanism of Action: (any)

Selected Parent Companies: (any)

Selected Subsidiary Companies: (any)

Selected Lifecycles: III; II

Selected Status Codes: Development; Inactive Development

Selected Countries: (any)

Prod. Reports: 3

| BrandID | Brand | Synonyms | Marketers | Compound Status |
|---|---|---|---|---|
| 5555 | irtemas | | Johanson | inactive dev. |
| 2321 | ER-90 | ER-90; urate oxidase; urate oxidaze | Sonoflow | development |
| 10021 | TM-87 | TM-87; Tele-201 | Tijan | development |

| LEVEL OF DETAIL: ☐ 1ST + ☐ 2ND + ☐ 3RD + ☐ 4TH + ☐ 5TH |
|---|
| 636                                    ☐ SELECT ALL   ☐ DESELECT ALL |

| OPTIONS:    640 | | |
|---|---|---|
| ☐ TRADITIONAL  +<br>MEDICINE | ☐ NON-TRADITIONAL<br>MEDICINE | ☐ INCLUDE QUESTIONS<br>FOR YOUR PHYSICIAN |

GENERAL TABLE OF CONTENTS  642

LEVEL 1
- ☐ DIAGNOSIS
  - ☐ SYNONYMS
  - ☐ INCIDENTS
  - ☐ MORTALITY
  - ☐ How DIAGNOSED
  - ☐ MEANING OF DIAGNOSIS
- ☐ TESTS/SCREENS FOR DIAGNOSIS
  - ☐ TEST INDICATIONS
- ☐ TREATMENT/THERAPY ALT.
  - ☐ [GEOGRAPHIC PULL-DoWN]
  - ☐ LOCAL
  - ☐ REGIONAL
  - ☐ U.S.
  - ☐ W.W.
  - ☐ EUROPE
  - ...
  - ☐ ASIA
- ☐ DRUGS
  - ☐ SIDE EFFECTS
  - ☐ TYPICAL DELIVERY REGIMENT
  - ☐ INTERACTIONS
  - ☐ CURRENT PRESCRIPTION COST
  - ☐ PACKAGE INSERTS
  - ☐ LOCAL PHARMACIES
  - ☐ WWW PHARMACIES
- ☐ HEALTHCARE PLAN COVERAGE
- ☐ ALTERNATIVE MEDICATIONS
- ☐ MEDICAL EQUIP AND SUPPLIES
  - ☐ [GEOGRAPHIC PULL-DoWN]
- ☐ PROGNOSIS

LEVEL 2
- ☐ PRACTITIONERS
  - ☐ [GEOGRAPHIC PULL-DOWN]
  - ☐ PRACTITIONER RATINGS
- ☐ CARE FACILITIES
- ☐ MEDICAL CENTERS
  - ☐ [GEOGRAPHIC PULL-DoWN]
  - ☐ MEDICAL CENTER RATINGS
- ☐ NURSING HOMES
  - ☐ [GEOGRAPHIC PULL-DoWN]
  - ☐ NURSING HOME RATINGS
- ☐ HOMECARE

LEVEL 3
- ☐ ARTICLES RELATING TO THE DIAGNOSIS AND PROGNOSIS
- ☐ THOUGHT LEADERS
  - ☐ [GEOGRAPHIC PULL-DoWN]
  - ☐ THOUGHT LEADER RATINGS
- ☐ THOUGHT LEADER CENTERS
  - ☐ [GEOGRAPHIC PULL-DOWN]
  - ☐ THOUGHT LEADER CTR RATINGS

LEVEL 4
- ☐ CLINICAL STUDIES
  - ☐ [GEOGRAPHIC PULL-DoWN]
  - ☐ QUALIFICATIONS
  - ☐ ApPLICATION PROCEDURE
- ☐ SUPPORT GROUPS
  - ☐ [GEOGRAPHIC PULL-DOWN]
  - ☐ SUPPORT GROUP RATINGS
- ☐ VIDEO CLIPS

LEVEL 5 (AVAIL IN PROF'L VER. ONLY)
- ☐ CONFERENCES
  - ☐ [GEOGRAPHIC PULL-DoWN]
  - ☐ CONFERENCE RATlNGS
- ☐ ASSOCIATIONS
  - ☐ [GEOGRAPHIC PULL-DoWN]
  - ☐ ASSOCIATION RATINGS

| TRANSMIT SELECTIONS | 644 |

DETAILED TABLE OF CONTENTS

DIAGNOSIS
   ☐ CORONARY DISEASE REPORT

_658_

TESTS/SCREENS FOR DIAGNOSIS

☐ ELECTROCARDIAGRAM REPORT
☐ STRESS TEST REPORT
☐ NUCLEAR SCANNING REPORT
☐ CORONARY ANGIOGRAPHY REPORT

MEDICAL CENTERS
   LOCAL TO STAMFORD, CT

☐ GREENWICH HOSPITAL CAPABILITIES REPORT
☐ STAMFORD HOSPITAL CAPABILITIES REPORT
☐ NORWALK HOSPITAL CAPABILITIES REPORT

| TRANSMIT SELECTIONS |
|---|

SYSTEM AND METHOD FOR CREATING A BOOK OF REPORTS OVER A COMPUTER NETWORK

CROSS REFERENCE TO RELATED APPLICATION

This application claims priority to provisional Patent Application Ser. No. 60/186,851 filed Mar. 2, 2000.

BACKGROUND OF THE INVENTION

1. Field of the Invention

The present invention relates generally to a system and method for generating and transmitting a book of reports over a computer network, and, more particularly, to a system and method for enabling a user to generate/retrieve related reports to form a book of reports concerning a particular subject matter, and transmit the book of reports to the user.

2. Background of the Related Art

There are literally thousands of Web sites ("sites") on the Internet that provide information related to the healthcare industry. The sites range from those that are oriented toward researchers involved in research and development of drug products, to manufacturers and retailers of medical equipment and products, to healthcare providers, to consumers. The uses for the information available on the Internet are as varied as the number of users that seek the information.

As an example, professionals involved in research and development of the latest pharmaceutical products may turn to sites such as Pharmaprojects Online (www.ovid.com), Pharmaceutical News Index (www.ovid.com), or DataStar-Web (products.dialog.com/products/datastarweb) to obtain information relevant to their research. On the other hand, healthcare providers in clinics or hospitals may turn to sites such as MedMarket.com (www.medmarket.com) for information concerning operating room products or testing equipment, or BuyMed.com (www.buymed.com) for information concerning more mundane medical products such as stethoscopes and walkers. Furthermore, consumers seeking information related to an illness, injury, or their general health may turn to sites such as Tufts Nutrition Navigator® (navigator.tufts.edu) for nutrition information or National Health Information Center (nhic-nt.health.org) for information concerning how to get in touch with healthcare professionals.

In searching for, retrieving, and organizing information found on the Internet, there are significant shortcomings in the present systems and methods that are available. For example, when drug researchers conduct research on the Internet to determine a market in which they should develop a new drug, they must collect vast quantities of information from a myriad of resources and carefully prepare a comprehensive, yet well organized catalogue of data. The ultimate decision as to how the development project should proceed depends in great part on the completeness, accuracy, and understandability of the collected information.

An analogous situation arises when a consumer conducts research on the Internet to obtain information concerning an illness, injury, or his general health. During the consumer's research, numerous sites may be reviewed to obtain a collection of articles, reports, and related information. Thereafter, the information is printed out. The consumers must then spend a significant amount of time sifting and sorting through the printed information to organize and decipher the material.

Of course, for both researchers and consumers, it would be preferable if the time spent on searching for, gathering, and organizing the information were applied to actually reading and scrutinizing the information itself. However, at the present time, the information must first be searched for, gathered, and organized before any meaningful review can be conducted.

Attempts have been made to simplify the process of searching for, gathering, and organizing information from the Internet and other database sources by researchers. For example, BizInt Smart Charts for Pharmaceuticals (BizInt Solutions, Orange, Calif.) is a program that provides a user the ability to download information and organize it into tabular reports. However, there are a limited number of sources from which the information may be obtained. In addition, the system runs on a standalone computer, therefore, all information that is to be organized must first be retrieved, for example, from sources on the Internet, and downloaded into the program. Furthermore, the output is a collection of reports. That is, the program does not provide any mechanism for organizing the resulting reports. Consequently, a user is left with a significant amount of work including searching for and collecting information, downloading the collected information into the program, and organizing the resulting reports that are output by the program.

Attempts have also been made to reduce the complexity of collecting and organizing information from the Internet by consumers. For example, the site drkoop.com® (www-.drkoop.com) provides a variety of healthcare related information. The site includes healthcare news, commentary from professionals in the industry, and other health related resources scattered throughout the site. A significant disadvantage of the site is that a consumer has to search throughout the entire site in order to find information relating to his interest. In addition, there is no facility for organizing the information that is found.

The site WebMD.com (www.webmd.com) also provides a variety of healthcare related information. As with the drkoop.com®, WebMD.com includes healthcare news, commentary from professionals in the industry, and other health related resources scattered throughout the site. WebMD.com includes basically the same disadvantages as drkoop.com® in that the consumer has to search throughout the entire site in order to find information relating to his interest. In addition, there is no facility for organizing the information that is found.

From the above, it is understood that a system and method is needed to more effectively assist professionals and consumers to focus their searches for information over the Internet. In addition, a system and method is needed to allow professionals and consumers to quickly review and organize their search results. Furthermore, a system and method is needed that is easy to operate and readily integrated into the various technical systems and methods presently employed by professionals and consumers.

SUMMARY OF THE DISCLOSURE

One embodiment of the present invention for creating and transmitting a book of reports over a computer network includes a method wherein a server receives from a user at least two report definitions and instructions to store the at least two report definitions in a storage device. Thereafter, the user may instruct the server to create a book with which the at least two report definitions are to be associated. In response, the server associates the at least two report definitions with the book. The user may then request that the server generate and transmit the book to his client. At such time, the server generates a report for each of the at least two report definitions associated with the book, which results in a book of reports. Subsequently, the book of reports is transmitted to the user.

The user may create the report definitions using, for example, a report definition routine and a product query routine. The report definition routine includes routines selected from the group including a filters routine, a columns routine, a countries routine, and an options routine. The filters routine includes routines selected from the group including a diagnosis filter routine, an MOA filter routine, a marketer filter routine, a lifecycle filter routine, and a status filter routine. A report definition created by the report definition routine produces a chart when processed by the server.

The product query routine includes routines selected from the group including a diagnosis filter routine, an MOA filter routine, a marketer filter routine, a lifecycle filter routine, a status filter routine, and a countries routine. A report definition created by the product query routine produces a product specification when processed by the server.

A table of contents including titles of the reports for the book can be generated by the server and transmitted to the user. Alternatively, descriptive headings in each report can be formatted prior to transmitting the book of reports to the user. After the book of reports has been transmitted to the user, the descriptive headings can be extracted and arranged to form a table of contents for the book of reports by the user's client.

Another embodiment of the present invention for creating and transmitting a book of reports over a computer network includes a method wherein a server receives a query for reports from a user. The server searches its databases and files to generate a general table of contents, which includes category headings related to the query for reports. The general table of contents is transmitted to the user.

The user selects category headings from the general table of contents and transmits his selection to the server. The server then searches its databases and files to generate a detailed table of contents, which includes titles of reports related to the selected category headings. The detailed table of contents is transmitted to the user. The user then selects particular reports from the detailed table of contents and transmits his selection to the server. The user may then transmit a request for one or more reports from the book of reports to the server.

Further embodiments of the present invention that are disclosed herein include systems for carrying out the above described methods. It is important to note that a variety of "reports" can be generated utilizing the systems and methods disclosed herein including documents, articles, abstracts, product specifications, charts, still images, video clips, and audio clips.

These and other unique features of the system and method disclosed herein will become more readily apparent from the following detailed description taken in conjunction with the drawings.

BRIEF DESCRIPTION OF THE DRAWINGS

So that those of ordinary skill in the art to which the subject invention pertains will more readily understand how to make and use the system and method described herein, preferred embodiments of the invention will be described in detail with reference to the drawings, wherein:

FIG. 1 is a block diagram illustrating a system for generating and transmitting a book over a computer network;

FIG. 2 is a flow chart depicting an embodiment of a method for generating and transmitting a book over a computer network;

FIG. 3A illustrates a book that was generated and transmitted by a system and method of the present invention;

FIGS. 3B and 3C illustrate a table of contents and a report in the form of a chart, respectively, that were generated utilizing an embodiment of the present invention;

FIGS. 8C-8G illustrate dialog boxes used in the filter routine steps of the report definition filters routine illustrated in FIGS. 8A and 8B;

FIGS. 10B and 10C illustrate product query dialog boxes used in the select criterion step illustrated in FIG. 10A and an example of the results of a product query, respectively;

FIG. 15A illustrates a general table of contents used to select/deselect the categories of information that may be included in a personalized book generated utilizing the embodiment of the present invention illustrated in FIG. 12;

FIG. 15B illustrates a detailed table of contents used to select/deselect the specific reports that may be included in a personalized book generated utilizing the embodiment of the present invention illustrated in FIG. 12;

DETAILED DESCRIPTION OF THE PREFERRED EMBODIMENTS

Figure 4:
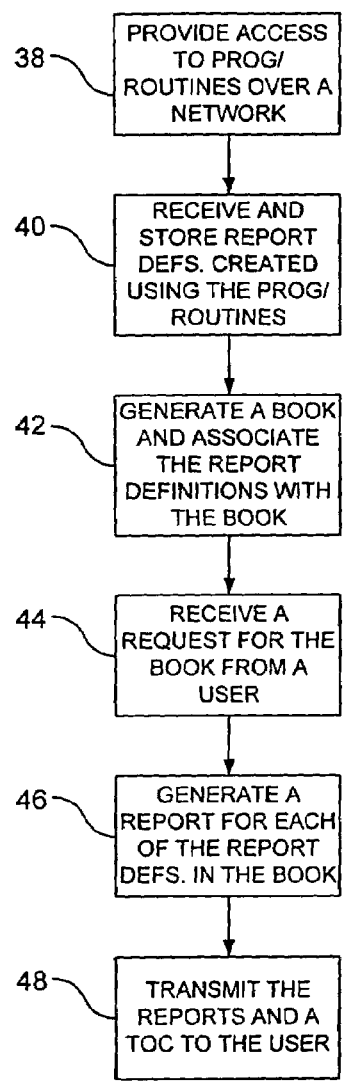
FIG. 4 is a flow chart depicting an embodiment of a method for generating and transmitting a book over a computer network.

Reference is now made to the accompanying Figures for the purpose of describing, in detail, the preferred embodiments of the present invention. The Figures and accompanying detailed description are provided as examples of the invention and are not intended to limit the scope of the claims appended hereto.

The present invention is directed to a data processing system and method for generating and transmitting a book of reports over a computer network. The system and method is intended to assist professionals and consumers in focusing their searches for information over the Internet. In addition, the system and method is intended to allow professionals and consumers to review and organize their search results. Furthermore, the system and method is intended to enable the professionals and consumers to transmit relevant portions of the search results as a book of reports to professionals and consumers. Still further, the system and method is intended to be easy to operate and readily integrated into the various systems and methods presently employed by professionals and consumers.

For the description that follows, the term "report" shall be defined as any collection of information concerning a particular subject matter. Examples of reports include documents, articles, abstracts, paragraphs, specifications, charts, still images, video clips, and audio clips. A report may be associated with a definition that defines the information that is to be included in the report and may define how the information is to be presented. For example, a report definition may be used to generate a chart or specification. The term "book definition" shall be defined as including a collection of related reports concerning a particular subject matter. Related reports may be listed in a table of contents ("TOC").

Reports in a book may be related in any number of ways. For example, reports in a book may be related by a complicated definition such as the "factors that contributed to the destabilization of economic models in non-democratic states." Such a book may include charts and statistical analyses illustrating the economic trends of eastern Europe after the fall of communism. Furthermore, the book may include scholarly publications discussing the cultures of each non-democratic state throughout the world. In this example, the charts, statistical analyses, and scholarly publications are all considered "reports."

Reports in a book may be related by a relatively simple definition such as "reports concerning Ford® automobiles sold in the U.S. during the year 1990." Such a book may include specifications describing each 1990 automobile manufactured by Ford®, articles from automotive magazines, images of each car for that year, and video and audio clips of car advertisements. In this example, the specifications describing each 1990 automobile manufactured by Ford®, articles from automotive magazines, images of each car for that year, and video and audio clips of car advertisements are all considered "reports."

The term "user" or "system user" shall refer to a person that interfaces with the system of the present invention. Typically, system users will directly interface with the system. For example, a system user may interface with the present invention over a network of computer systems such as the Internet using a client/server model. The term "client" shall refer to a computer that includes a processor, storage, display, and an input and output device. Clients utilize the services of "servers".

In the remainder of the detailed description of the preferred embodiments, only subject matter related to the healthcare industry are referred to in exemplifying the present invention. Those of ordinary skill in the art will readily appreciate that other subject matter (e.g., economics and automobiles) may be included in a system and method of the present invention.

Referring to FIG. 1, a block diagram depicts a system 10 configured in accordance with the present invention. The system 10 includes a server 12 operated by an administrator 13 and in communication with one or more storage devices 14. The storage device 14 contains proprietary databases 16, files 18, and programs/routines 20. In addition, server 12 is in communication via a network 22 with sites 24 from which other databases, files, and programs/routines can be downloaded. Also in communication with the server 12 via the network 22 are one or more clients 26 operated by users 28.

More specifically, the server 12 is in communication via the network 22 with site #24(1), site #24(2), etc. In addition, the server 12 is in communication via the network 22 with client 26(1) which is operated by user 28(1), client 26(2) which is operated by user 28(2), etc.

Those of ordinary skill in the art will appreciate that various types of network 22 schemes are available and include, but are not limited to, connection to the Internet via modems and Internet host, direct Internet connections via routers, hard-wired point-to-point connections, radio communications, optical communications, and combinations of the aforementioned.

Those of ordinary skill in the art will also appreciate that server 12 may be configured to store data in one or more internal storage devices, one or more external storage devices, or a combination of internal and external storage devices. The external storage devices may be local or remote to server 12. In addition, the storage devices of the present invention may be of any type known in the art (e.g., floppy disk, hard disk, compact disk ("CD"), digital video disk ("DVD"), tape drive, etc.)

Although the databases 16, files 18, and programs/routines 20 are illustrated to be stored in a single storage device 14, those of ordinary skill in the art will readily appreciate that the data may be stored in disparate storage devices. Unless otherwise specified, references herein to a storage device include permanent and/or volatile storage.

In addition, those of ordinary skill in the art will recognize that although the data bases 16, files 18, and programs/routines 20 are particularly described herein, they may assume other forms, arrangements, and/or configurations and should be considered to remain in keeping with the spirit and scope of the present invention.

FIG. 2 is a flow chart depicting an embodiment of a method for generating and transmitting a book over a computer network. In one example of the embodiment, a user 28 seeks reports on a particular subject matter such as an illness. At step 30, the user 28 uses a client 26 to access programs/routines 20 of a Web site through the server 12. Using the programs/routines 20, the user 28 searches the databases 16 and files 18 to retrieve titles of reports relating to the particular subject matter. At step 32, the titles are collected to form a book definition. The titles may be organized in the book definition as desired by the user 28. The collection of titles forms the basis of a table of contents. At step 34, the book, including a table of contents and the reports, is transmitted from the server 12 to the client 26.

If the user 28 desires, he may print the table of contents and/or one or more reports at his own computer. Alternatively, the user 28 may submit a request for the administrator 13 to print the table of contents and/or one or more reports at the server 12. The latter alternative may be preferable, for example, when the user 28 wants to print a book that includes a substantial number of reports. The latter alternative may also be preferable when the user 28 wants to print a book that includes reports having color graphs, charts, and/or images and he does not have a color printer.

FIG. 3A illustrates a book 36 generated by the system and method of the present invention. The book includes a table of contents wherein report titles are categorized. For example, Report #1 is categorized under Category A, Report #2 is categorized under Category A, Report #3 is categorized under Subcategory A, etc. The system and method is sufficiently flexible so that any number of categories, subcategories, and report titles may be included in a table of contents to form a book.

FIG. 3B illustrates a table of contents for a book that was generated utilizing an embodiment of the present invention. The table of contents includes the titles of reports related to a particular subject matter. Such a table of contents and the reports identified therein may be generated and transmitted to a user utilizing an embodiment of the present invention as described herein.

FIG. 3C illustrates a report in the form of a chart which was generated utilizing an embodiment of the present invention as described herein. The title of the chart may be included as part of a book having the table of contents illustrated in FIG. 3B. Such a chart may be generated by, for example, business development, licensing, market research, and R&D personnel in the pharmaceutical industry to identify potential business development and licensing opportunities. Further details concerning generation of the chart are included herein below.

FIGS. 4-11B illustrate an embodiment ("first embodiment") of the present invention. More specifically, FIG. 4 includes a flow chart illustrating an overview of the embodiment, while FIGS. 5-11B illustrate routines that may be implemented to carry out the embodiment. The embodiment may include the system 10 as illustrated in FIG. 1. The embodiment is intended to provide business development, licensing, market research and R&D personnel in the pharmaceutical industry the ability to quickly access, extract and report on any combination of request criterior. A multiple number of related reports may be generated and readily organized to create a book. The book may include a table of contents identifying the collection of related reports. To support the embodiment, the databases 16 include product, business, financial, and scientific information on thousands of marketed products and compounds in development. A purpose of the embodiment is to quickly and efficiently identify potential business development and licensing opportunities.

Referring to FIGS. 1 and 4, the first embodiment of the present invention may be described generally as follows. It is notable that the flow chart in FIG. 4 is from the perspective of the server 12. At step 38, a user 28 accesses programs/routines 20 at a Web site on the server 12 with his client 26. At step 40, the user 28 creates report definitions for charts, specifications and other types of reports concerning a particular subject matter utilizing the programs/routines 20 and transmits them to the server 12 for storage. Each report definition is identified by a report title. At step 42, the user 28 creates and stores a book on the server 12 and has the report definitions associated with the book. The titles of the report definitions can be displayed on the user's client 26 as a table of contents for the book, for example, so the contents of the book can be edited. At step 44, the user transmits a request for the book to the server 12. At step 46, the server generates the reports based on the report definitions associated with the book and, at step 48, transmits the reports to the user's client 26. The server may also transmit the table of contents for the book to the client 26. Alternatively, the reports may include formatting that facilitates creation of the table of contents by the user's client 26. The user 28 may print and/or store the book of reports.

Figure 5A:
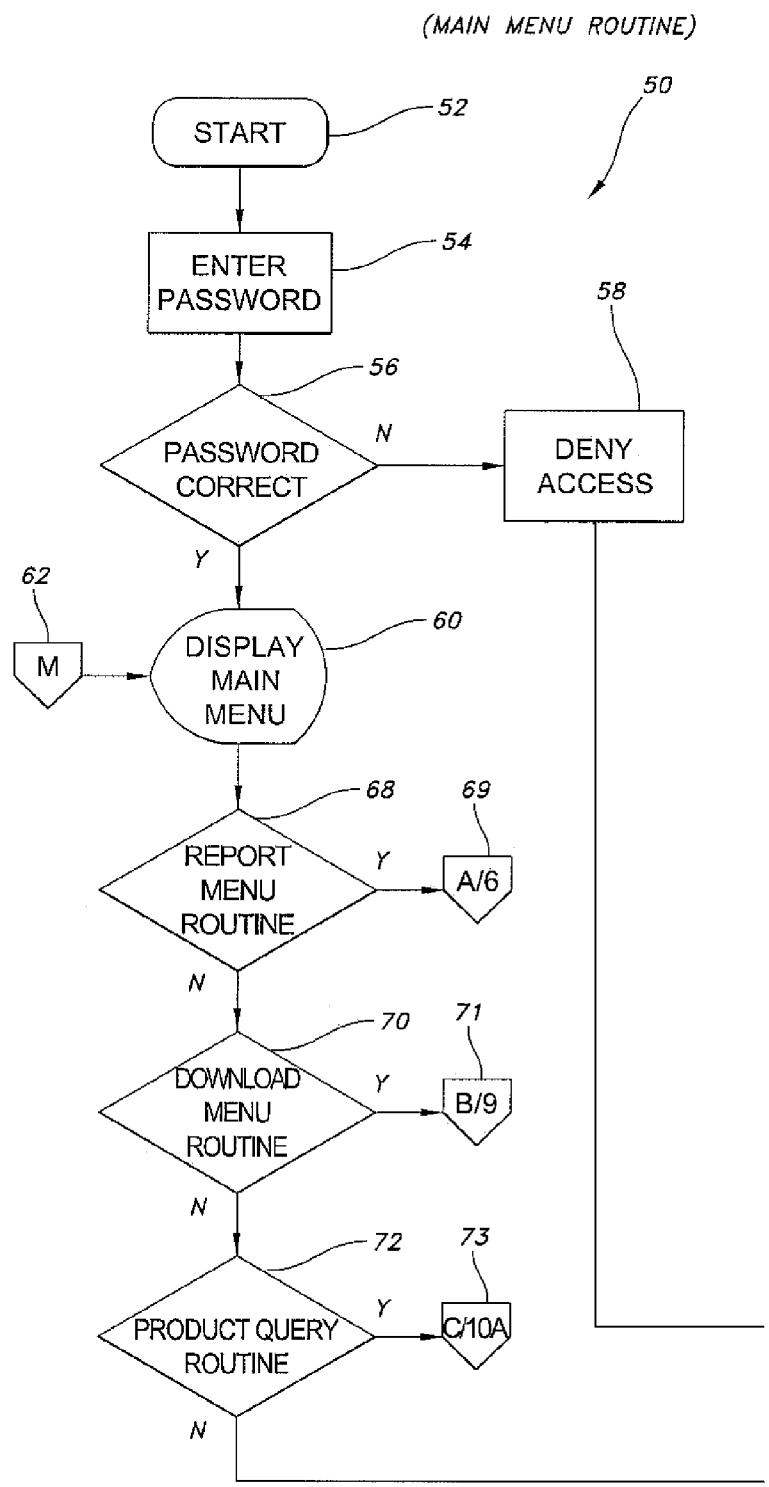
FIGS. 5A and 5B illustrate a flow chart of a main menu routine used in the embodiment of the present invention illustrated in FIG. 4.
Figure 5B:
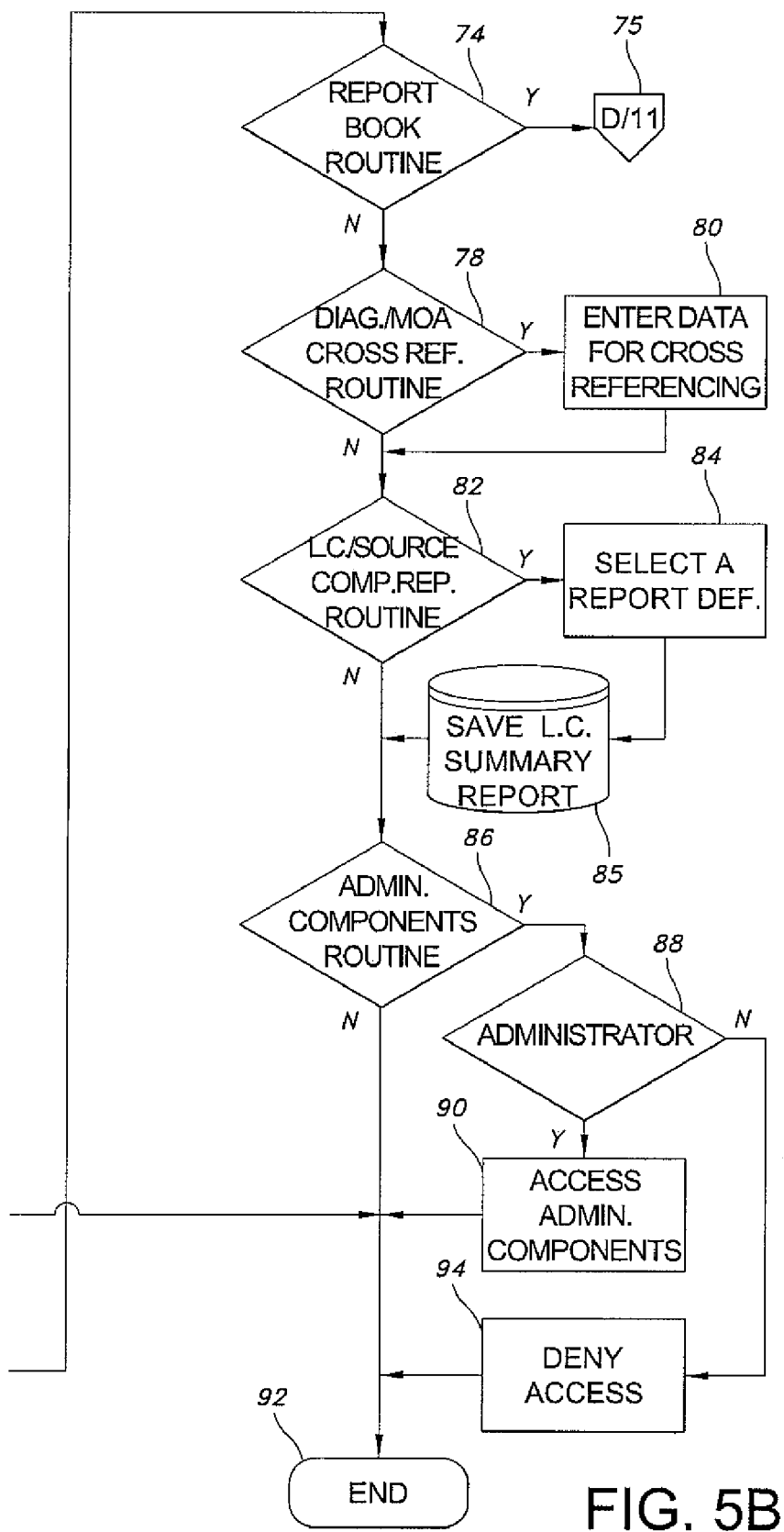

Referring to FIGS. 5A and 5B, a flow chart of a software routine 50 for a main menu used in the above-described embodiment is illustrated. Main menu routine 50 provides access to a report menu routine 100 (FIG. 6) at step 68, a download menu routine 300 (FIG. 9) at step 70, a product query routine 350 (FIG. 10A) at step 72, a report book routine 400 (FIGS. 11A and 11B) at step 74, a diagnosis/mechanisms-of-action cross reference routine at step 78, a life-cycle/source comparison report routine at step 82, and an administrative components routine at step 86. Each routine is more fully discussed herein below.

At step 52, a user accesses the site and, at step 54, enters a password for obtaining access to routine 50. If, at step 56, the password is not accepted, then access to the system is denied at step 58. If, at step 56, the user's password is accepted, then, at step 60, a main menu is displayed on the user's display. Connector M as shown in step 62 is provided to allow other routines to return to the main menu routine 50.

For clarity, each connector, except for the main menu connector M, includes a numeric character for identifying the figure on which a mating connector is found. For example, connector "A/6" at step 69 in FIGS. 5A and 5B has a mating connector "A/5" at step 102 in FIGS. 6A and 6B.

At step 68, the system determines whether the report menu routine 100 was selected. If the routine was selected, the system proceeds to routine 100 (FIGS. 6A and 6B) at step 69 (connector A). If routine 100 was not selected, the system proceeds to step 70. At step 70, the system determines whether the download menu routine 300 (FIG. 9) was selected. If routine 300 was selected, the system proceeds to routine 300 at step 71 (connector B). If routine 300 was not selected, the system proceeds to step 72.

At step 72, the system determines whether the product query routine 350 was selected. If the routine was selected, the system proceeds to routine 350 (FIG. 10A) at step 73 (connector C). If routine 350 was not selected, the system proceeds to step 74. At step 74, the system determines whether the report book routine 400 (FIGS. 11A and 11B) was selected. If the routine was selected, the system proceeds to routine 400 at step 75 (connector D). If routine 400 was not selected, the system proceeds to step 78.

At step 78, the system determines whether the diagnosis/mechanism-of-action cross reference routine was selected by the user. If the routine was selected, the system proceeds to step 80 where the user is prompted to either enter/select a diagnosis to obtain all mechanisms-of-action ("MOA") associated with the diagnosis or enter/select an MOA to obtain all diagnoses associated with the MOA. Thereafter, the system proceeds to step 82. If, at step 78, the routine was not selected, the system proceeds directly to step 82.

At step 82, the system determines whether the life-cycle/source comparison report routine was selected by the user. If the routine was selected, the system proceeds to step 84 where the user is prompted to select a report definition for which a life-cycle summary report may be generated. The life-cycle summary report is a chart that includes drug source companies correlated with the life-cycles of the companies' drugs which satisfy the criterior of the report definition. After the user selects a report definition, the system generates the life-cycle summary report and, at step 85, stores the report in the storage device 14. Thereafter, the system proceeds to step 86. If, at step 82, the routine was not selected, then the system proceeds directly to step 86.

At step 86, the system determines whether the administrative components routine was selected. If the routine was selected, then the system proceeds to step 88. At step 88, the system determines whether an administrator selected the administrative components routine. If the system was selected by an administrator 13, then the system proceeds to step 90 where the administrator 13 may access various administrative components of the system such as creating/editing company profiles, user profiles, drug details, etc. Thereafter, the system proceeds to step 92 to end the session. If, at step 88, the system determines that the routine was selected by a user, then access is denied at step 94. Thereafter, the system proceeds to step 92 to end the session. If, at step 86, the system determines that the administrative components routine was not selected, then the system proceeds directly to step 92 to end the session.

Figure 6A:
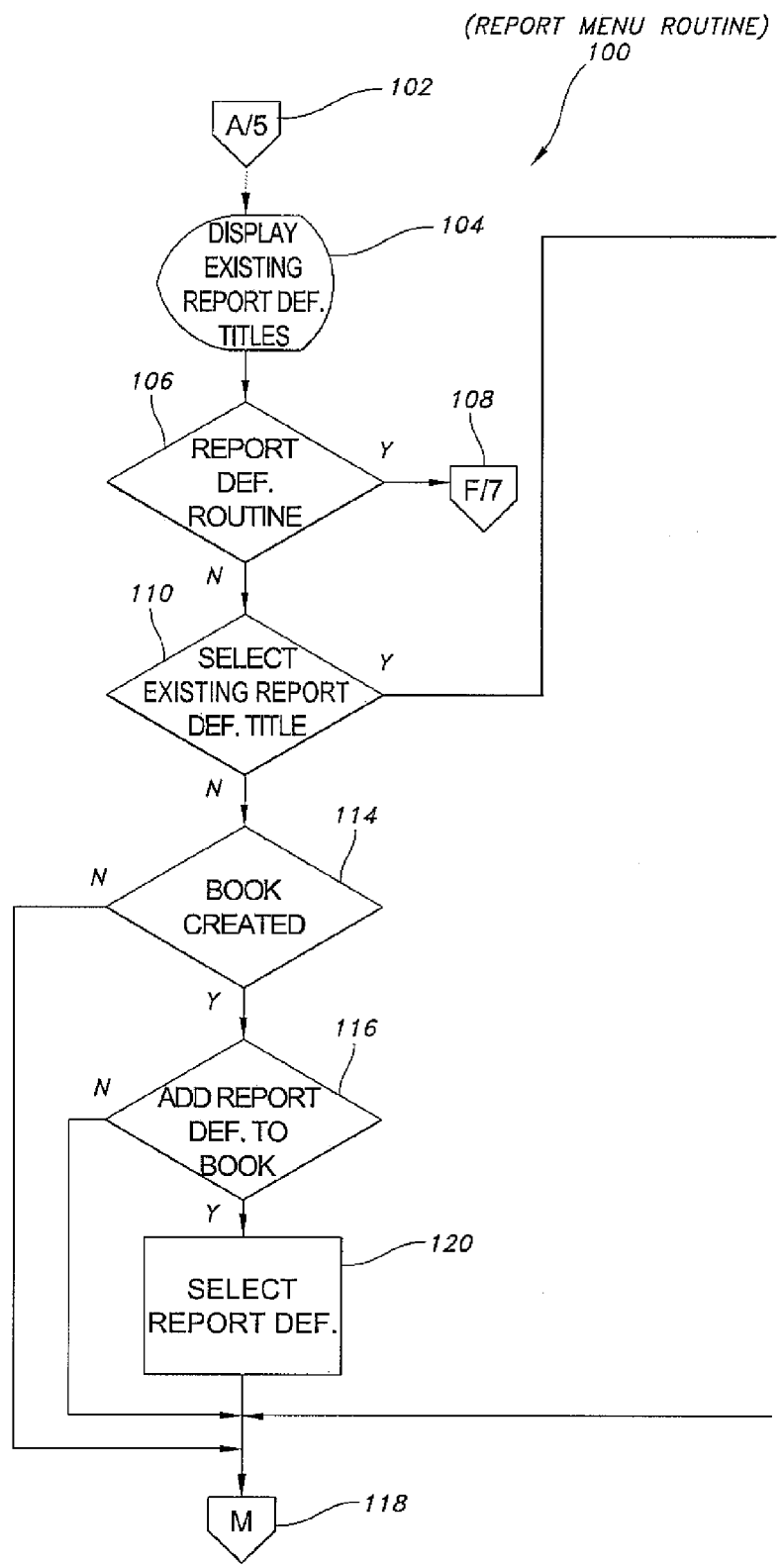
FIGS. 6A and 6B illustrate a flow chart of a report menu routine used in the embodiment of the present invention illustrated in FIG. 4.
Figure 6B:
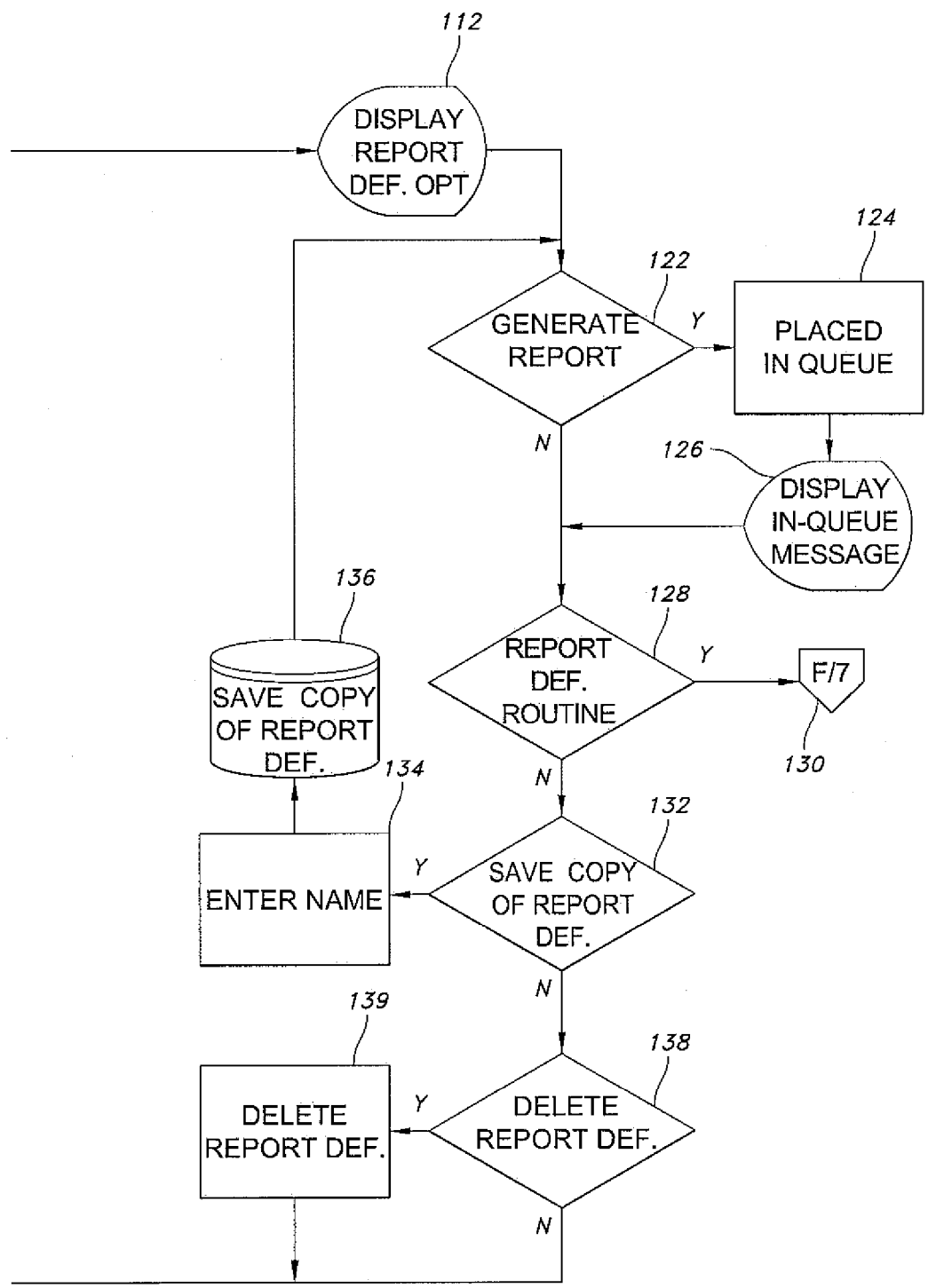

Referring to FIGS. 6A and 6B, a flow chart illustrates the report menu routine 100. At step 102 (connector A), a user enters routine 100 from the main menu routine 50 and proceeds to step 104. At step 104, a menu is displayed which includes a list of titles of report definitions that were previously created and stored. As noted above, a report definition defines the information that is to be included in a report and may define how the information is to be presented.

At step 106, the system determines whether a report definition routine 140 (FIGS. 7A and 7B) was selected by the user to create a new report definition. If routine 140 was selected, the system proceeds to routine 140 at step 108 (connector F). If routine 140 was not selected, then the system proceeds to step 110. At step 110, the system determines whether a title of an existing report definition was selected by the user from the list of titles. If a title was selected, then the system proceeds to step 112 where the selected report definition identified by the title is made active. If a title was not selected, then the system proceeds to step 114.

At step 114, the system determines whether a book was previously created by the user. If a book was previously created and the user selects it to make it active (these processes are described in more detail herein below), then the system proceeds to step 116. At step 116, the system determines whether the user selected to add a report definition to the active book. If so, then the system proceeds to step 120. At step 120, the user selects a title of a report definition that is to be added to the active book. The system automatically adds the selected report definition to the active book. Thereafter, the user may return to the main menu routine 50 at step 118 (connector M). If, at step 116, the user did not select to add a report definition to the active book, then the user returns directly to the main menu routine 50 at step 118 (connector M). If, at step 114, a book was not previously generated, then the user may return to the main menu routine 50 at step 118 (connector M).

At step 112, the system displays various options available to the user for processing the active report definition. At step 122, the system determines whether the user selected to generate a report defined by the active report definition. If the user selected to generate a report, then the system proceeds to step 124. At step 124, the system retrieves the report definition and places it in the queue for processing. Thereafter, at step 126, the system displays an "in-queue" message to the user to indicate that the request has been queued for processing. The user may then proceed to step 128. If, at step 122, the system determines that the user did not select to generate a report, then the system proceeds directly to step 128.

At step 128, the system determines whether the report definition routine 140 (FIGS. 7A and 7B) was selected by the user to edit the active report definition. If routine 140 was selected, then the system proceeds to routine 140 at step 130 (connector F). If routine 140 was not selected, then the system proceeds to step 132. At step 132, the system determines whether a copy of the active report definition is to be saved. If a copy is to be saved, then the user enters a name for the copy at step 134, and, at step 136, the copy is saved to storage. Thereafter, the system returns to step 122. If, at step 132, the user does not desire to create a copy of the active report definition, then the system proceeds to step 138.

At step 138, the system determines whether the user selected to delete the active report definition. If the active report definition is to be deleted, the system proceeds to step 139 and deletes the active report definition. Thereafter, the user may return to the main menu routine 50 at step 118 (connector M). If, at step 138, the active report definition is not to be deleted, then the system proceeds to the main menu routine 50 at step 118 (connector M).

Figure 7A:
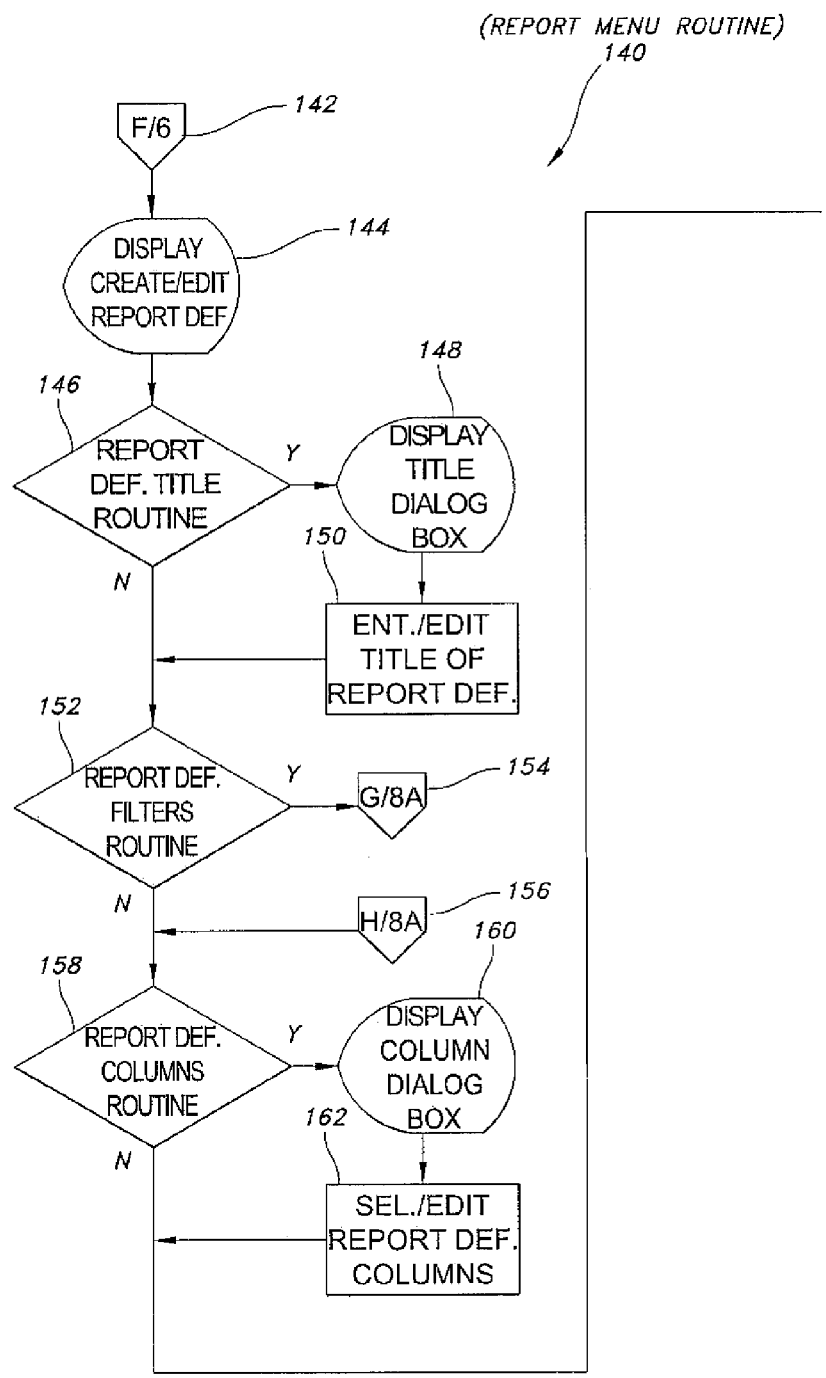
FIGS. 7A and 7B illustrate a flow chart of a report definition routine used in the embodiment of the present invention illustrated in FIG. 4.
Figure 7B:
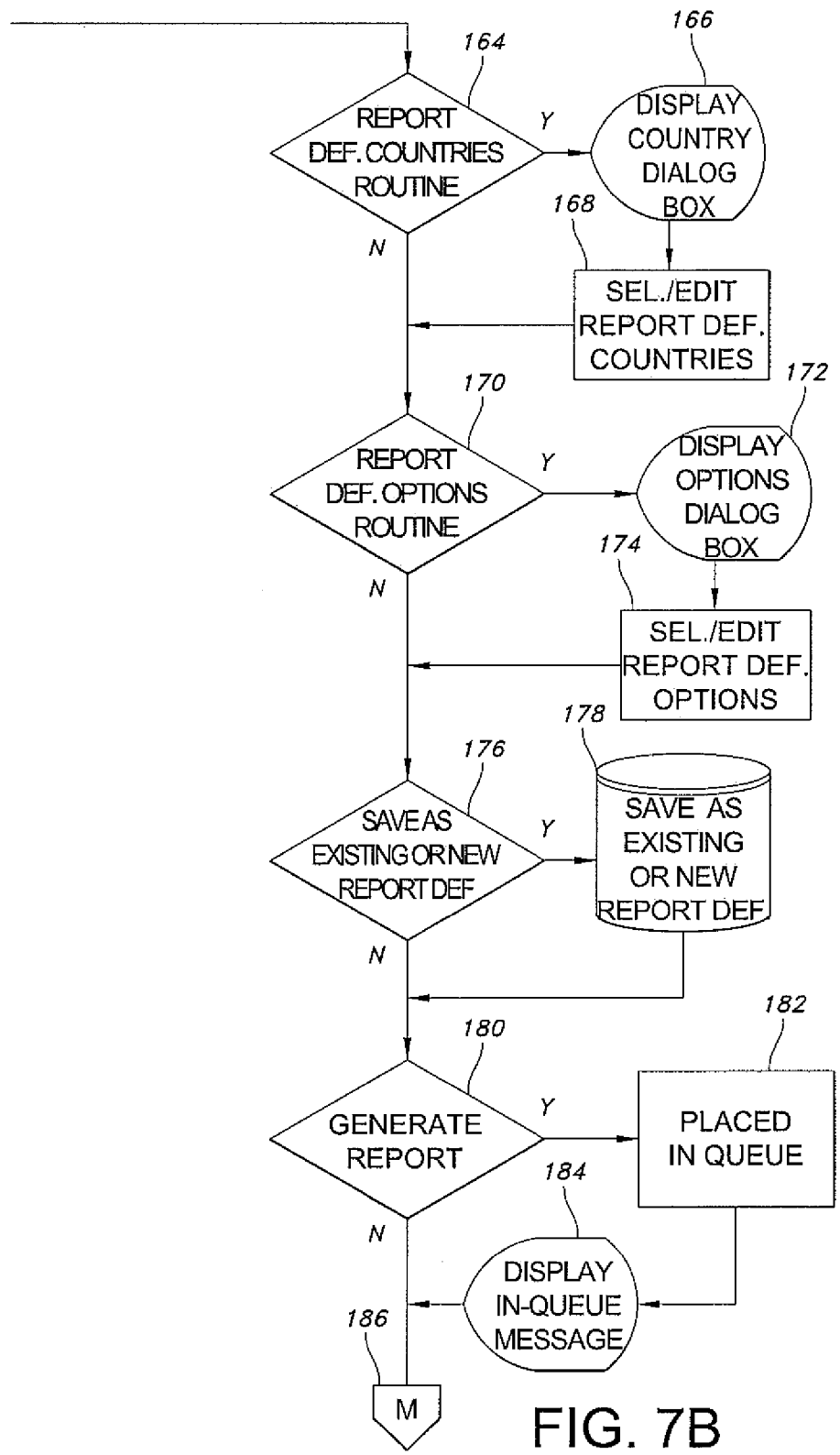

Referring to FIGS. 7A and 7B, a flow chart illustrates the report definition routine 140. The report definition routine 140 is particularly useful for creating or editing a report definition for a chart. At step 142 (connector F), a user enters routine 140 from either step 108 of routine 100 (FIGS. 6A and 6B) to create a report definition or step 130 of routine 100 to edit an existing report definition, and proceeds to step 144. At step 144, a menu is displayed to the user which includes options for creating or editing a report definition. At step 146, the system determines whether the user selected a report definition title routine. If the routine was selected, then a title dialog box is displayed at step 148 and, at step 150, the user enters/edits the title of the report definition. For example, the user that generated the report illustrated in FIG. 3C entered the title "Angiogenesis Mechanisms of Action Report—U.S. Products in Development." After entering/editing a title, the user may proceed to step 152. If, at step 146, the user does not select the report definition title routine, then the system proceeds directly to step 152.

Figure 8A:
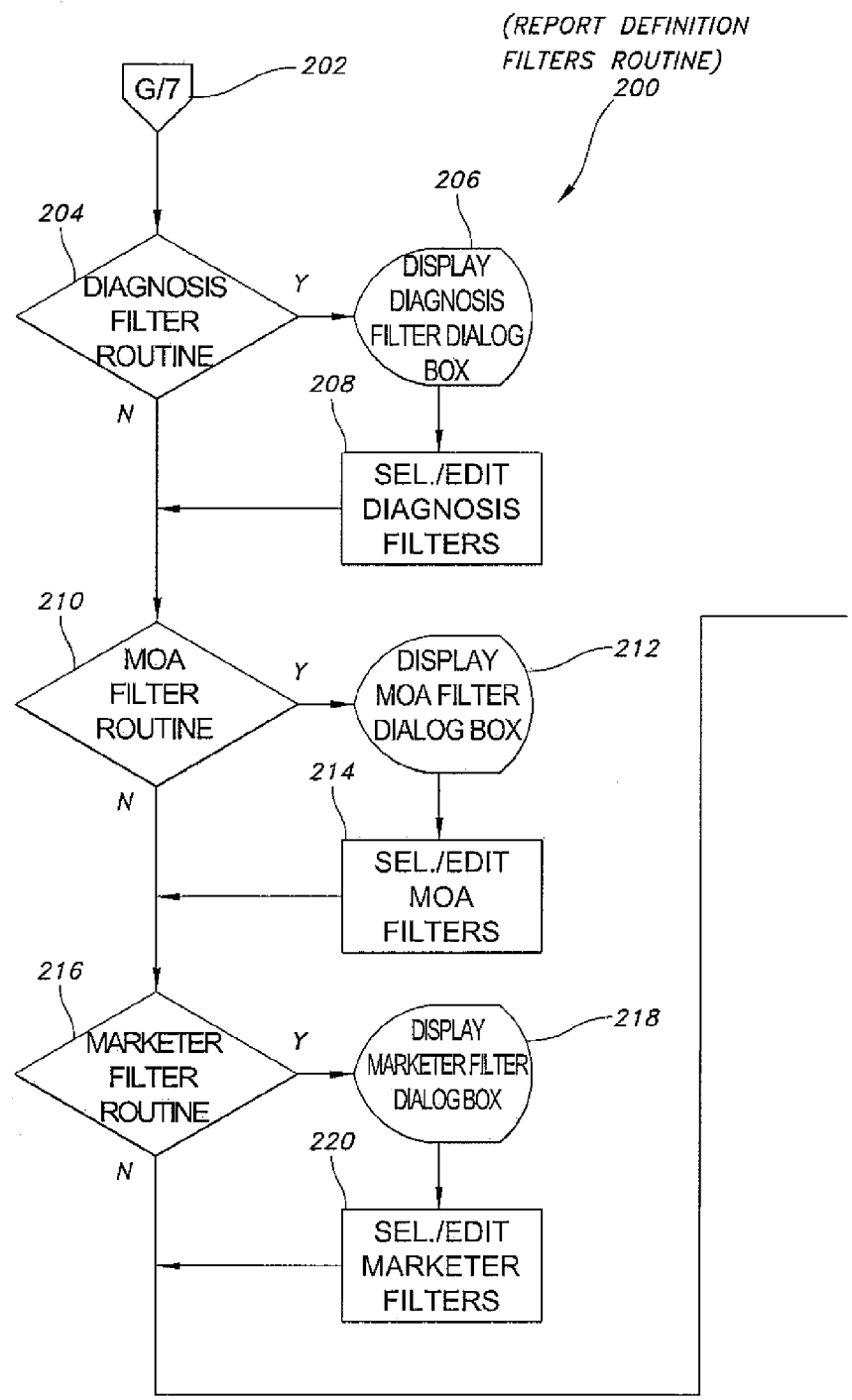
FIGS. 8A and 8B illustrate a flow chart of a report definition filters routine used in the embodiment of the present invention illustrated in FIG. 4.
Figure 8B:
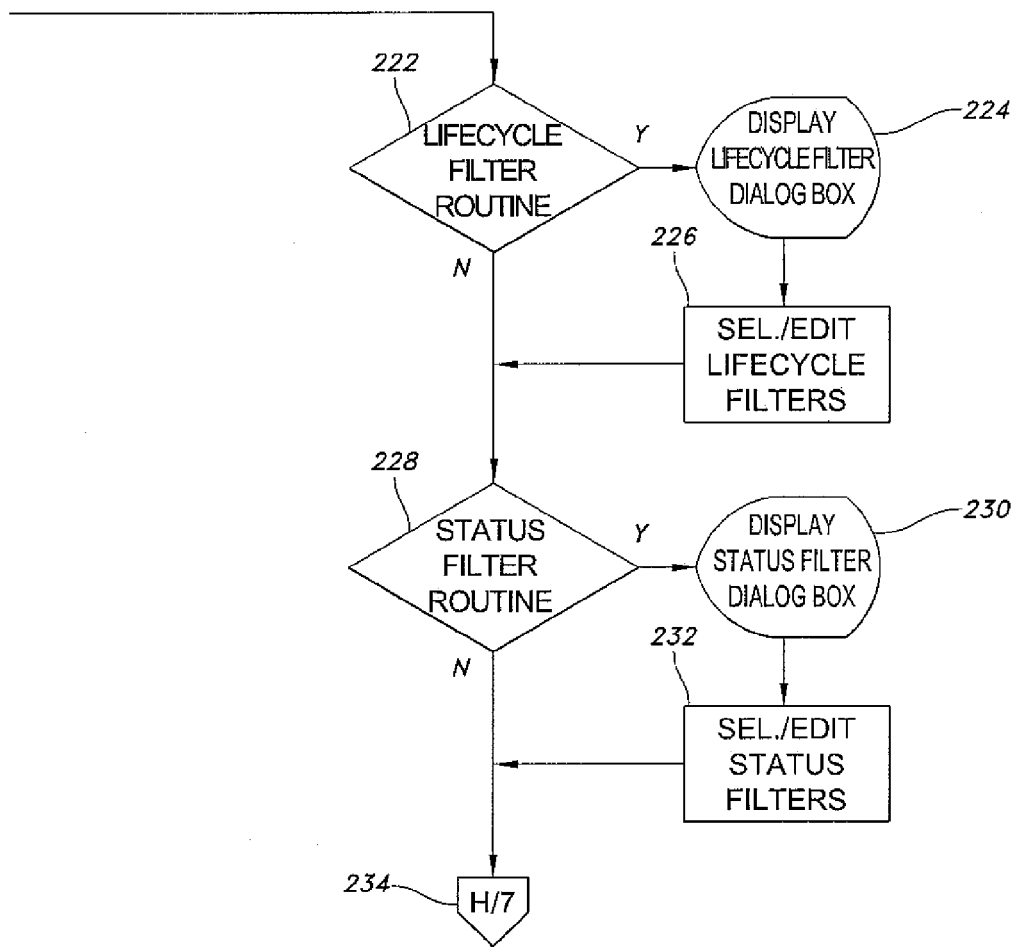

At step 152, the user is prompted to select a report definition filters routine 200 (FIGS. 8A and 8B). If routine 200 was selected, the system proceeds to routine 200 at step 154 (connector G). If routine 200 was not selected, then the system proceeds to step 158. At step 158, the system determines whether the user selected a report definition columns routine. If the routine was selected by the user, then a dialog box is displayed at step 160 and, at step 162, the user selects/edits the columns that are to be included in the chart.

For example, the user that generated the report illustrated in FIG. 3C selected/edited the report definition so that the parent company, subsidiary company, licensors, brand name, generic/synonym names, MOA, and diagnoses columns appear in the report. (The remaining columns, i.e., brand ID, lifecycle, licensing opportunity, and pipeline status (based on MOA) columns, were selected using other routines as described below.) After selecting/editing the columns, the user may proceed to step 164. If, at step 158, the user did not select the report definition columns routine, then the system proceeds directly to step 164.

At step 164, the system determines whether the user selected a report definition countries routine. If the user selected the routine, a dialog box is displayed at step 166 and, at step 168, the user selects/edits the countries that are to be included. For example, the user that generated the report illustrated in FIG. 3C selected/edited the report definition so that lifecycle and licensing opportunities would appear for drugs in development in the United States (i.e., "US Lifecycle" and "US Lic Opp") and for drugs in development throughout the world that lack specific country detail (i.e., "WW Lifecycle" and "WW Lic Opp".) After selecting/editing the countries, the user may proceed to step 170. If, at step 164, the user does not select the report definition countries routine, then the system proceeds directly to step 170.

At step 170, the user is prompted to select a report definition options routine. If the user selects the routine, then a dialog box is displayed at step 172 and, at step 174, the user selects/edits the report definition options. The options may include selecting a report's grid type, wherein the selection dictates the report's header selection, i.e., either: 1) diagnoses group(s), diagnoses subgroup(s), and/or diagnoses; or 2) therapeutic group(s), mechanism of action subgroup(s), and/or mechanism of action. Additional options may include suppressing blank grid columns, showing sales totals, and showing pipeline total rows. Furthermore, options may be included to generate a related pipeline summary sheet, a lifecycle summary sheet, or a licensing opportunities sheet. After selecting/editing the report definition options, the user may proceed to step 176. If, at step 170, the user did not select the report definition options routine, then the system proceeds directly to step 176.

At step 176, the system determines whether the user selected to save the report definition as an existing file or as a new file. If the user selected to save the report definition, then the system proceeds to step 178 and the report definition is saved to storage. Thereafter, the user may proceed to step 180. If, at step 176, the user did not select to save the report definition, then the system proceeds directly to step 180.

At step 180, the system determines whether the user selected to generate a report defined by the active report definition. If the user selected to generate a report, then the system retrieves the report definition and places it in the queue for processing at step 182. At step 184, an "in-queue" message is displayed to the user to indicate that the request has been queued for processing. Thereafter, the user may return to the main menu routine 50 at step 186 (connector M). If, at step 180, the user did not select to generate a report, then the user may proceed directly to the main menu routine 50 at step 186 (connector M).

Referring to FIGS. 8A and 8B, a flow chart illustrates the report definition filters routine 200. At step 202 (connector G), a user enters routine 200 from step 154 of routine 140 (FIGS. 7A and 7B). At step 204, the system determines whether the user selected a diagnosis filter routine. If the routine was selected by the user, a dialog box is displayed at step 206 and, at step 208, the user selects/edits diagnosis filters to add to the report definition.

The diagnosis filters may include categories such as diagnosis groups, diagnosis subgroups, and individual diagnoses. For example, a diagnosis group may be identified as dermatological disorders; a related diagnosis subgroup identified as dermatitis; and related individual diagnoses identified as atopic, general allergic, contact, non-allergic, and seborrhoeic dermatitis. As a further example, a diagnosis group may be identified as infectious diseases; a related diagnosis subgroup identified as fungal diseases; and related individual diagnoses identified as blastomycosis, candidiasis, fungal infection, and mycosis. As a more particular example, the diagnosis group oncology was selected in developing the chart in FIG. 3C.

FIGS. 8C and 8D illustrate a series of dialog boxes that may be utilized at step 208 to select/edit diagnosis filters. Initially, a diagnosis filters box 250 is displayed. To select/edit diagnosis groups, a user pulls down a select diagnosis groups box 251 from the diagnosis filters box 250 and selects one or more diagnosis groups. To select/edit diagnosis subgroups, the user pulls down a select diagnosis subgroups box 252 from the diagnosis filters box 250 and selects a diagnosis group from a pull-down menu 253. Upon selecting a diagnosis group, a dialog box 254 appears which includes all diagnosis subgroups related to the selected diagnosis group. The user selects one or more diagnosis subgroups from the dialog box 254. To select/edit an individual diagnoses, the user pulls down a select individual diagnoses box 255 from the diagnosis filters box 250 and enters search text to find individual diagnoses. Upon entering the search text, a dialog box 256 appears including the individual diagnoses. The user selects one or more individual diagnoses from the dialog box 256. All selected diagnosis filters are displayed under their respective headings in diagnosis filters box 250.

Returning to FIGS. 8A and 8B, at step 208, after selecting/editing the diagnosis filters to include as part of the report definition, the user may proceed to step 210. If, at step 204, the user did not select the diagnosis filter routine, then the system proceeds directly to step 210.

At step 210, the system determines whether the user selected an MOA filter routine. If the user selected the routine, a dialog box is displayed at step 212 and, at step 214, the user selects/edits MOA filters to add to the report definition. Similar to the diagnosis filters described above, the MOA filters may include categories such as MOA (i.e., therapeutic) groups, MOA subgroups, and individual MOA. As a particular example, the individual MOAs angiogenesis inhibitor, angiogenesis stimulant, and angiogenesis inducer were utilized in developing the chart in FIG. 3C.

FIGS. 8E and 8F illustrate a series of dialog boxes that may be utilized at step 214 to select/edit MOA filters. Initially, an MOA filters box 260 is displayed. To select/edit therapeutic groups, a user pulls down a select therapeutic groups box 261 from the MOA filters box 260 and selects one or more MOA groups. To select/edit MOA subgroups, the user pulls down a select MOA subgroups box 262 from the MOA filters box 260 and selects a therapeutic group from a pull-down menu 263. Upon selecting a therapeutic group, a dialog box 264 appears which includes all MOA subgroups related to the selected therapeutic group. The user selects one or more MOA subgroups from the dialog box 264. To select/edit an individual MOA, the user pulls down a select individual MOA box 265 from the MOA filters box 260 and enters search text to find individual MOAs. Upon entering the search text, a dialog box 266 appears including the individual MOAs. The user selects one or more individual MOAs from the dialog box 266. All selected MOA filters are displayed under their respective headings in MOA filters box 260.

Returning to FIGS. 8A and 8B, at step 214, after selecting/editing the MOA filters to include as part of the report definition, the user may proceed to step 216. If, at step 210, the user did not select the MOA filter routine, then the system proceeds directly to step 216.

At step 216, the system determines whether the user selected a marketer filter routine. If the user selected the routine, then a dialog box is displayed at step 218 and, at step 220, the user selects/edits marketer filters to add to the report definition. The marketer filters may include categories such as parent companies and subsidiary companies. After selecting/editing marketer filters to include as part of the report definition, the user may proceed to step 222. If, at step 216, the user did not select the marketer filter routine, then the system proceeds directly to step 222.

At step 222, the system determines whether the user selected a lifecycle filter routine. If the user selected the routine, then a dialog box is displayed at step 224 and, at step 226, the user selects/edits lifecycle filters to add to the report definition. A variety of lifecycle filters may be made available. For example, a first group of lifecycle filters may identify the development phase (e.g., preclinical, phase I, phase II, fast track, phase III, pre-registration, or registered) of a drug's lifecycle. A second group of lifecycle filters may identify the post-development phase (e.g., generic, patent protected, or patent expired) of a drug's lifecycle.

FIG. 8G illustrates a dialog box 270 that may be utilized at step 226 to select/edit lifecycle filters. A variety of lifecycle filters are illustrated including both pre-and post-development lifecycle filters. A user may select one or more of the lifecycle filters individually. In addition, a user may select all development phase lifecycle filters, i.e., filters "U", "TI", and "PC" through "R", using a "Development" button 272. Furthermore, a user may select all of the post-development phase lifecycle filters, i.e., filters "M" through "PT" using a "Marketed" button 274.

Returning to FIGS. 8A and 8B, at step 226, after selecting/editing lifecycle filters to be included as part of the report definition, the user may proceed to step 228. If, at step 222, the user did not select the lifecycle filter routine, then the system proceeds directly to step 228.

At step 228, the system determines whether the user selected a status filter routine. If the user selected the routine, then a dialog box is displayed at step 230 and, at step 232, the user selects/edits status filters to add to the report definition. A variety of status filters may be made available. For example, status filters may be included to identify over-the-counter, hospital, nutritional, and diagnostic products. After selecting/editing status filters to include as part of the report definition, the user may return to the report definition routine 140 at step 234 (connector H). If, at step 228, the user did not select the status filter routine, then the user may proceed directly to the report definition routine 140 at step 234 (connector H).

Figure 9:
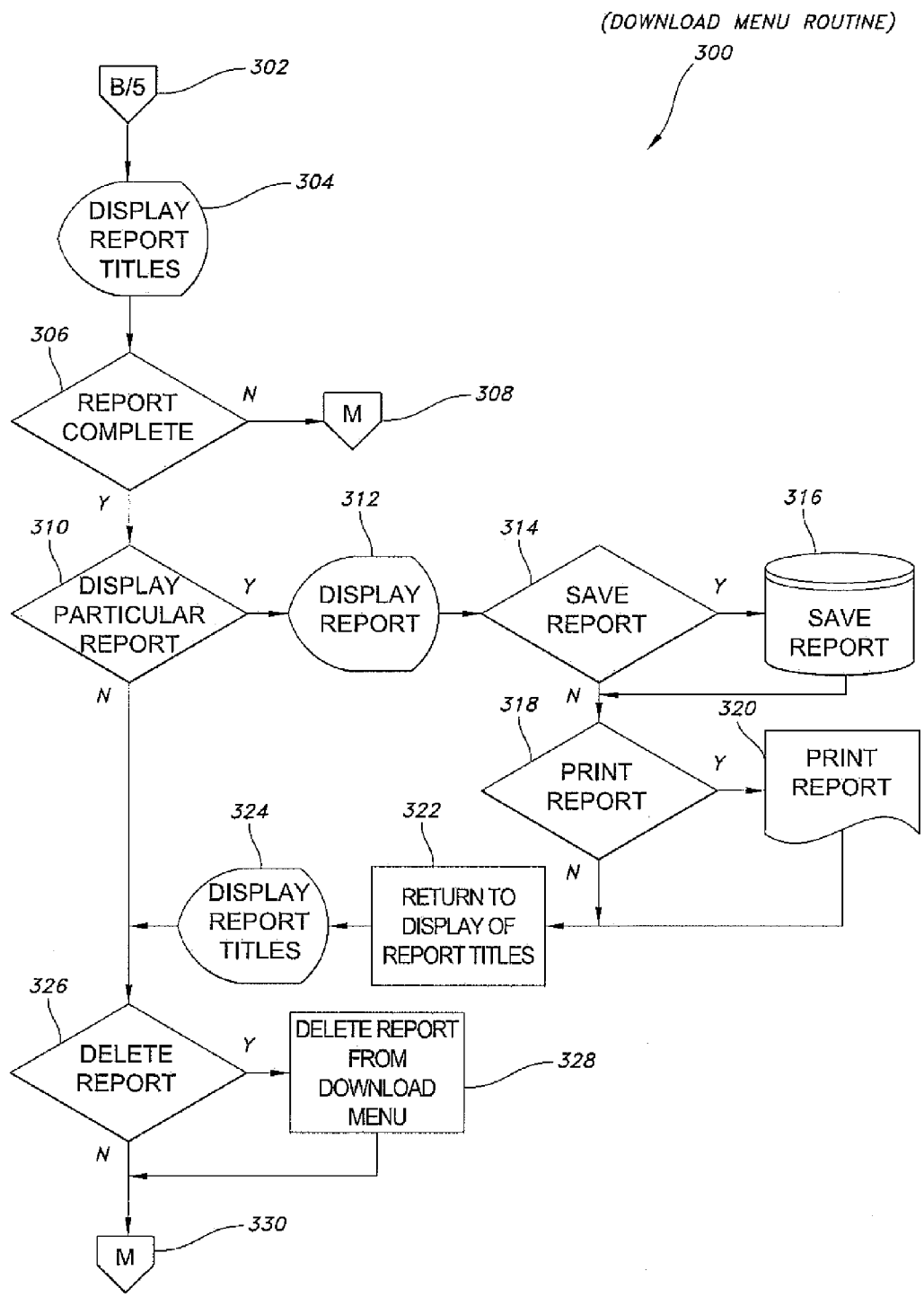
FIG. 9 illustrates a flow chart of a download menu routine used in the embodiment of the present invention illustrated in FIG. 4.

Referring to FIG. 9, a flow chart illustrates a download menu routine 300. At step 302 (connector B), a user enters routine 300 from routine 50 and proceeds to step 304. At step 304, a menu is displayed which includes a list of titles of report definitions that were previously placed in the queue to generate a report, for example, at step 124 (FIGS. 6A and 6B) and step 182 (FIGS. 7A and 7B). At step 306, the system determines whether the server has processed a report definition and a report has been generated. If the report is not generated, then the user may proceed to the main menu routine 50 at step 308 (connector M). If the report is generated, then the system identifies the generated report as complete and ready for download and proceeds to step 310.

At step 310, the system determines whether the user selected a completed report for display. If a completed report has been selected, then the server downloads the completed report to the client and the report is displayed to the user at step 312. At step 314, the user decides whether the report is to be stored on the client. If the user decides to store the report, then, at step 316, the report is stored on the client. Thereafter, the user proceeds to step 318. If, at step 314, the user decided not to store the report, then the user proceeds directly to step 318. At step 318, the user decides whether the report is to be printed by the client. If the user decides to print the report, then, at step 320, the client prints the report. Thereafter, at step 322, the user returns to the display of the report titles, for example, by retrieving the previous page. If, at step 318, the user does not decide to print the report, then the user may return directly to the display of the report titles at step 322. At step 324, the report titles are displayed to the user. Thereafter, the user proceeds to step 326. If, at step 310, the user did not select to display a particular report, then the system proceeds directly to step 326.

At step 326, the system determines whether the user has selected to delete a particular report from the report titles that are displayed. If the user selected to delete a particular report, then, at step 328, the particular report is deleted. It is notable that although the report is deleted, the report definition is not deleted and may be found through the report menu routine 100 (FIGS. 6A and 6B). After the particular report is deleted at step 328, the user may return to the main menu routine 50 at step 330 (connector M). If, at step 326, the user did not select to delete a report, then the user may proceed directly to the main menu routine 50 at step 330 (connector M).

Figure 10A:
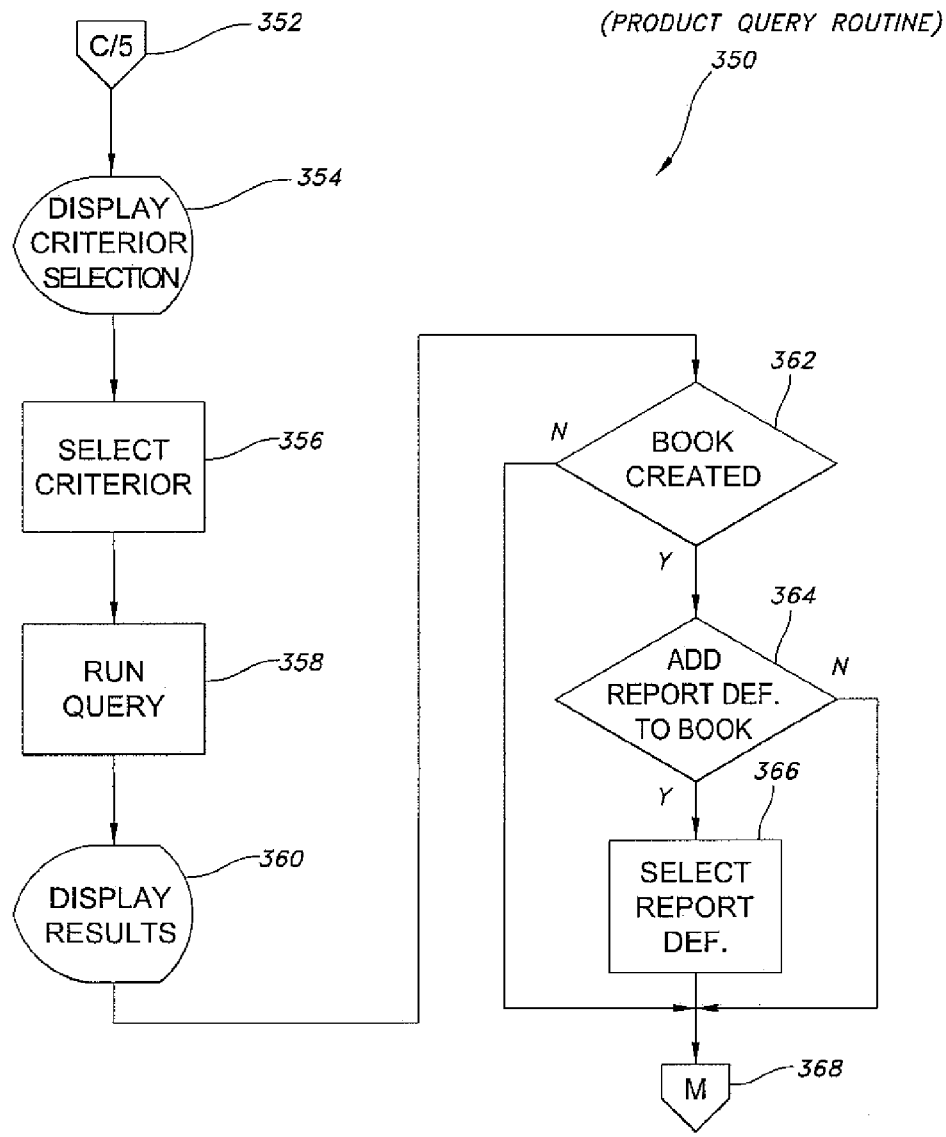
FIG. 10A illustrates a flow chart of a product query routine used in the embodiment of the present invention illustrated in FIG. 4.

Referring to FIG. 10A, a flow chart illustrates a product query routine 350. The product query routine 350 is particularly useful for searching for product reports. At step 352 (connector C), a user enters routine 350 from the main menu 50 and proceeds to step 354. At step 354, a menu is displayed which includes criterior selection dialog boxes. At step 356, the user selects report criterior utilizing the dialog boxes to create a query. Thereafter, the user proceeds to step 358 where he runs the query. The result of the product query is displayed at step 360.

FIG. 10B illustrates a series of dialog boxes that may be utilized at step 356 to search for product reports. Dialog box 370 functions similar to the diagnosis filters box 250 described herein above and illustrated in FIGS. 8C and D. Dialog box 372 permits a user to perform the functions described herein above at step 220 (FIGS. 8A and 8B). Dialog box 374 functions similar to the MOA filters box 260 described herein above and illustrated in FIGS. 8E and 8F. Dialog box 376 functions similar to the lifecycles filter box 270 described herein above and illustrated in FIG. 8G. Dialog box 378 permits the user to perform the functions described herein above at step 168 (FIGS. 7A and 7B). After selecting criterior to search for particular product reports, the user selects the "Run Query" button 380.

FIG. 10C illustrates the results displayed to a user after running a product query for one or more particular product reports. The product criterior in the query included: "gout" selected as the diagnosis; phases "II" and "III" selected as the lifecycles; and "development" and "inactive development" selected as the status codes. The product query resulted in retrieving the titles of report definitions of product reports for three drugs, namely, irtemas, ER-90, and TM-87.

Referring to FIG. 10A, at step 362, the system determines whether a book was previously created by the user. If a book was previously created and the user selects it to make it active, then the system proceeds to step 364. At step 364, the system determines whether the user selected to add a title of a report definition to the active book. If so, then the system proceeds to step 366. At step 366, the user selects a title of one or more report definitions that are to be added to the active book. The system automatically adds the selected titles to the active book.

Using the method described above, for example, the titles of the report definitions for irtemas, ER-90, and TM-87 (obtained in the example above using the product query routine 350 (FIG. 10A)) were added to the table of contents illustrated in FIG. 3B. It is notable that the table of contents includes titles of different types of reports, namely, the chart entitled "Angiogenesis Mechanisms of Action Report" and the three product reports for irtemas, ER-90, and TM-87.

After the titles of selected product reports have been added to the active book, the user may return to the main menu routine 50 at step 368 (connector M). If, at step 364, the user did not select to add one or more titles of product reports to the active book, then the user returns directly to the main menu routine 50 at step 368 (connector M). If, at step 362, a book was not previously created, then the user may return directly to the main menu routine 50 at step 368 (connector M).

Figure 11A:
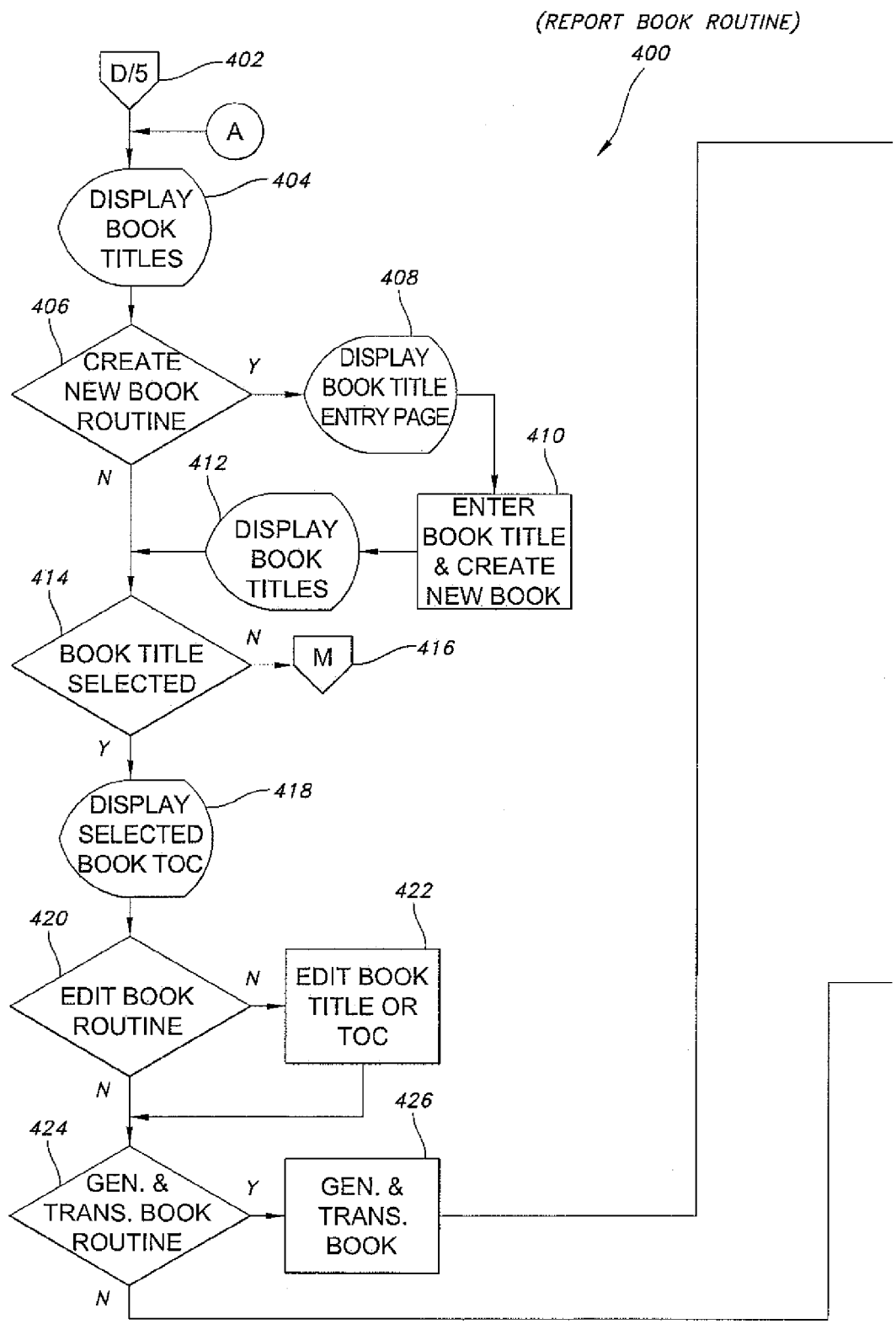
FIGS. 11A and 11B illustrate a flow chart of a report book routine used in the embodiment of the present invention illustrated in FIG. 4.
Figure 11B:
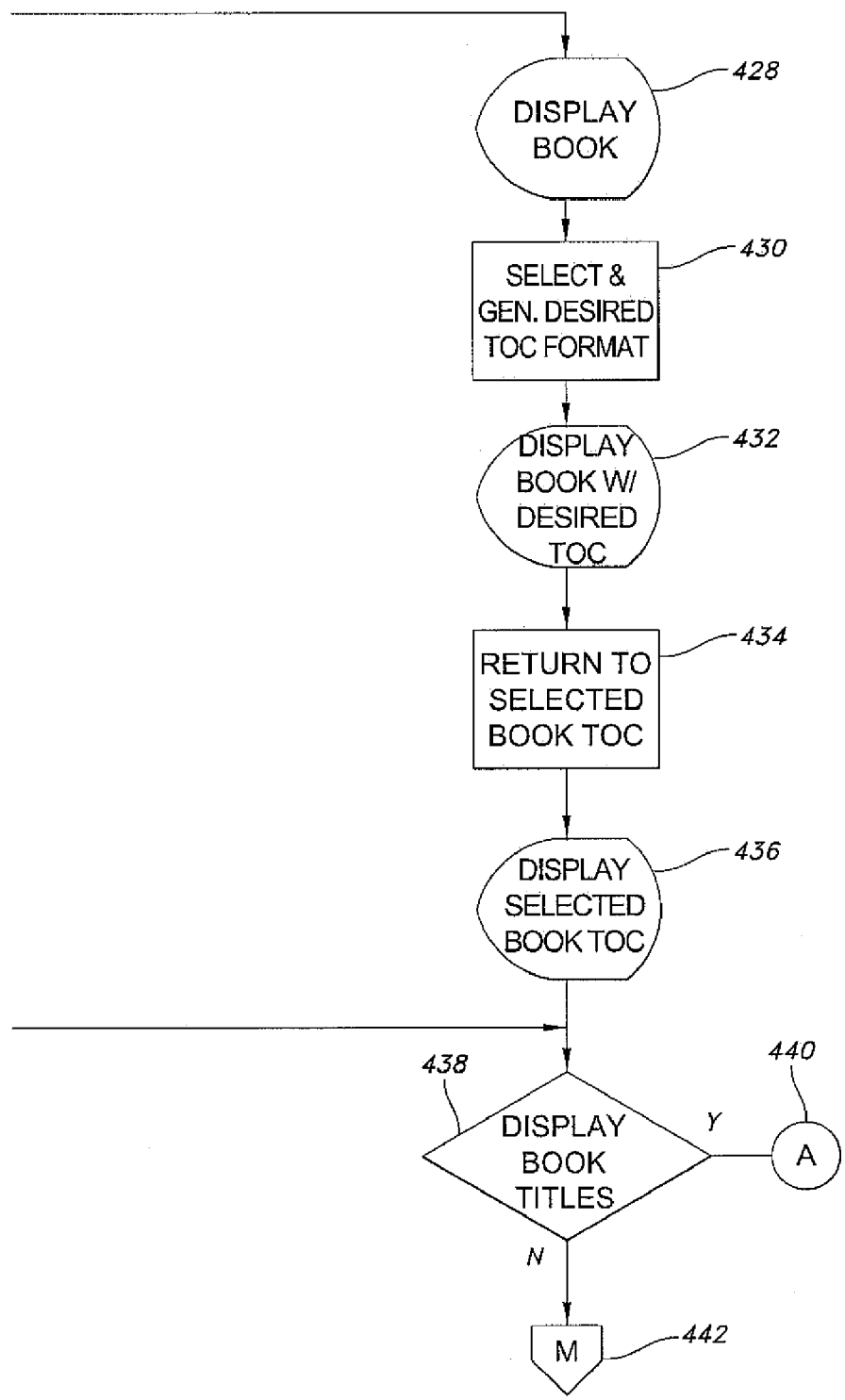

Referring to FIGS. 11A and 11B, a flow chart illustrates the report book routine 400. At step 402 (connector D), a user enters routine 400 from routine 50 and proceeds to step 404. At step 404, a menu is displayed which includes a list of the titles of books previously created by the user. At step 406, the system determines whether a create new book routine was selected by the user. If the routine was selected, then the system displays a book title entry page to the user at step 408. At step 410, the user enters the title for the new book and the system creates a new book. Thereafter, at step 412, the menu is displayed which includes the list of titles of books. The title of the book that was generated immediately above is now included in the list. The system then proceeds to step 414. If, at step 406, the user did not select the create new book routine, then the system proceeds directly to step 414.

At step 414, the system determines whether the user selected a book title to display its table of contents. If the user did not select a book title, then the user may proceed to the main menu routine 50 at step 416 (connector M). If a book title was selected, then, at step 418, the table of contents of the selected book is displayed. At step 420, the system determines whether an edit book routine was selected by the user. If the routine was selected, then, at step 422, various functions are made available to the user so that he may make a variety of edits to the book. For example, functions are available to edit the title of the book, list the report definitions in the table of contents alphabetically by title, list the report definitions in the table of contents as specifically defined by the user, and add/remove one or more report definitions to/from the book. Thereafter, the system proceeds to step 424. If, at step 420, the edit book routine was not selected, then the system proceeds directly to step 424.

At step 424, the system determines whether the user selected a generate and transmit book routine. If the routine was selected, then, at step 426, the system generates the book and transmits it to the client. The book includes each of the reports listed in the table of contents.

So that a table of contents may be created for the book at the client, descriptive headings in each report are appropriately formatted by the system prior to transmitting the book to the user. For example, a book having reports formatted in rich text format may have headings in such reports formatted by the system to conform with the index and tables routine provided in Microsoft® Word 97 (Microsoft Corp., Redmond, Wash.). In such case, a user whose client includes the Word 97 word processing program may receive the book of reports and readily create a table of contents therefor.

At step 428, the book is displayed to the user. At step 430, the user selects a format from an appropriate application program available on his client and generates a table of contents, for example, using the method described herein above, for the transmitted book. Thereafter, at step 432, the book, which now includes the completed table of contents and reports, is displayed on the client. The user may, of course, store and/or print the book using the client. At step 434, the user returns to the display of the table of contents of the selected book (viewed above at step 418 prior to transmittal of the book to the user), for example, by retrieving the previous page. At step 436, the table of contents of the selected book is displayed to the user. Thereafter, the system proceeds to step 438. If, at step 424, the user did not select the generate and transmit book routine, then the user may proceed directly to step 438.

At step 438, the system determines whether the user selected to view the list of the titles of the books generated by the user. If the user did select to view the list of book titles, then, at step 440 (connector A), the user is returned to step 404 where the menu is displayed which includes the list of the book titles. If, at step 438, the user did not select to view the list of book titles, then the user may proceed directly to the main menu routine 50 at step 442 (connector M).

FIGS. 12-17C illustrate another embodiment ("second embodiment") of the present invention. More particularly, FIG. 12 includes a flow chart illustrating an overview of the second embodiment and FIGS. 13A-17C illustrate routines for its implementation. The routines may be carried out on the system 10 illustrated in FIG. 1. The second embodiment described herein below pertains to the health care industry, however, those of ordinary skill in the art will appreciate that it may be adapted for use in other industries.

An advantage of the second embodiment is that it provides a consumer/professional in the healthcare industry the ability to quickly and efficiently retrieve and assemble a personalized book that includes reports relating to an injury, illness, or general healthcare matter as described by the consumer/professional. Another advantage of the second embodiment is that it promotes better communications between consumers and their professional healthcare providers. Still a further advantage of the second embodiment is that it improves consumers' and professionals' knowledge of various injuries, illnesses, and general healthcare matters. Other advantages will become apparent from the description provided herein below.

Figure 12:
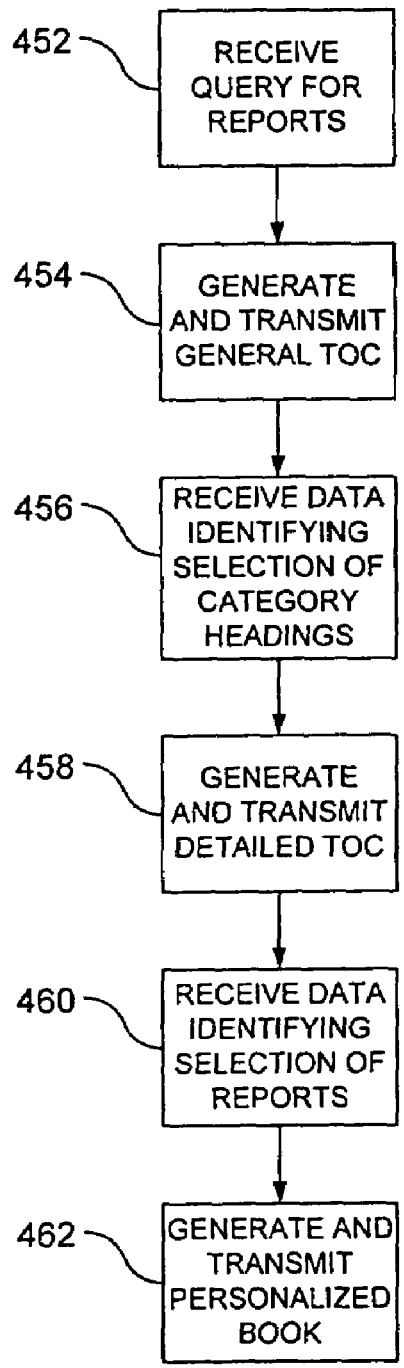
FIG. 12 is a flow chart depicting an embodiment of a method for generating and transmitting a book over a computer network.

Referring to FIGS. 1 and 12, the second embodiment of the present invention may be described generally as follows. It is notable that the flow chart in FIG. 12 is from the perspective of the server 12. A user 28 accesses a Web site on the server 12 which includes programs and routines 20 configured in accordance with the second embodiment of the present invention. At step 452, the user 28 transmits to the server 12 a query including information describing various aspects of his medical condition. The information may include, for example, descriptions of the user's medical profile, proscription drug use, and healthcare insurance. At step 454, a general table of contents is generated on the server 12, and thereafter transmitted to and displayed on the user's client 26. The general table of contents includes category headings that relate to the information provided by the user 28.

At step 456, the user 28 selects one or more of the category headings from the general table of contents and transmits his selections to the server 12. At step 458, a detailed table of contents is generated on the server 12, and thereafter transmitted to and displayed on the user's client 26. The detailed table of contents includes the category headings selected by the user and titles of reports that relate to the selected category headings. An abstract of each report may also be included. At step 460, the user 28 selects one or more of the reports from the detailed table of contents and transmits his selection to the server 12. At step 462, a personalized book is generated based on the book contents selected by the user and transmitted to the user's client 26 for viewing and printing. The personalized book includes the reports corresponding to the selected titles of reports, and may include a table of contents listing the selected category headings and the selected titles of reports.

The query for reports, selected category headings, and titles of selected reports constitute a "book definition" for the user's personalized book. The book definition may be given a title, stored in the storage device 14, and subsequently retrieved by the user 28 for editing.

Figure 13A:
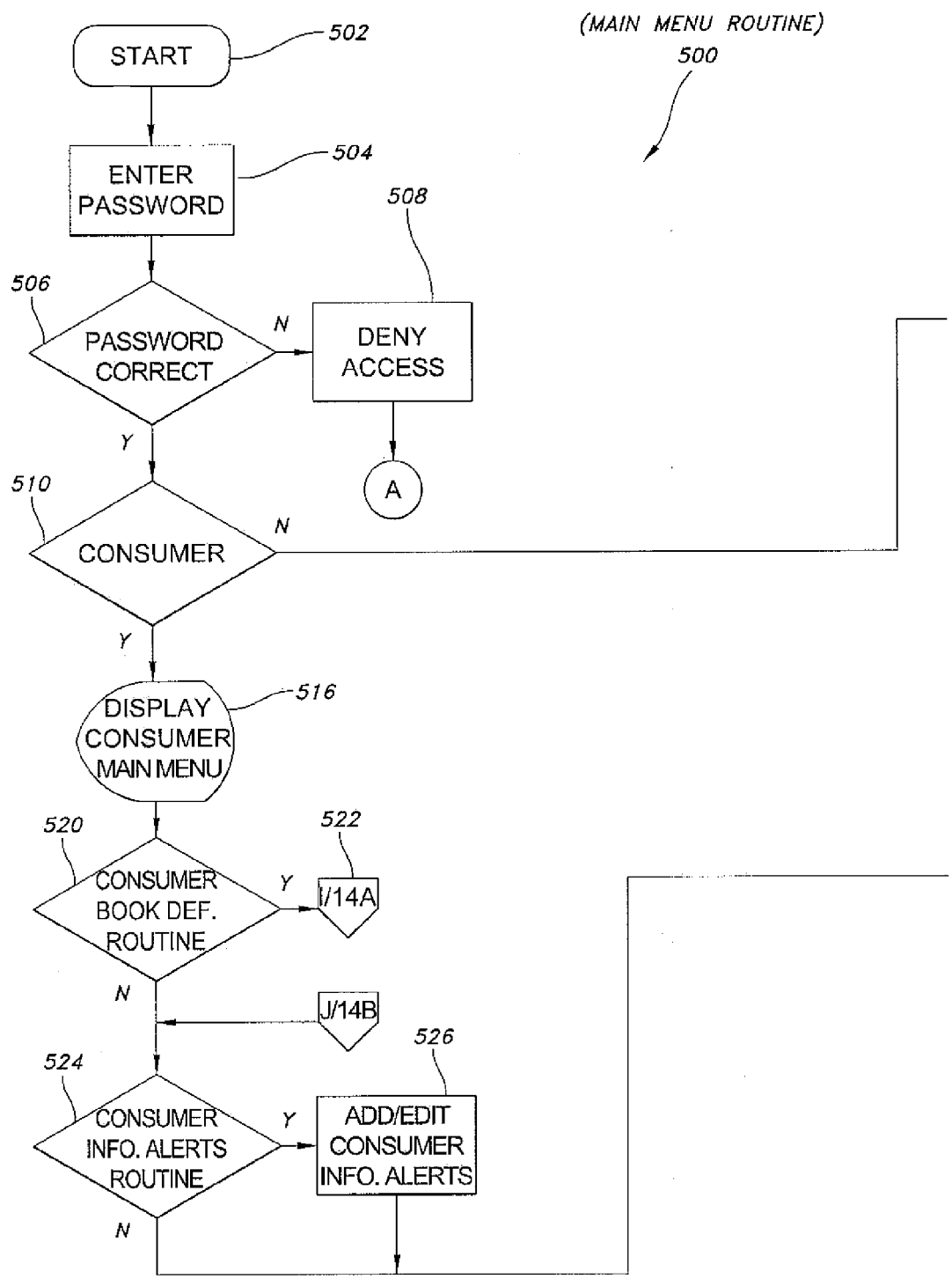
FIGS. 13A and 13B illustrate a flow chart of a main menu routine used in the embodiment of the present invention illustrated in FIG. 12.
Figure 13B:
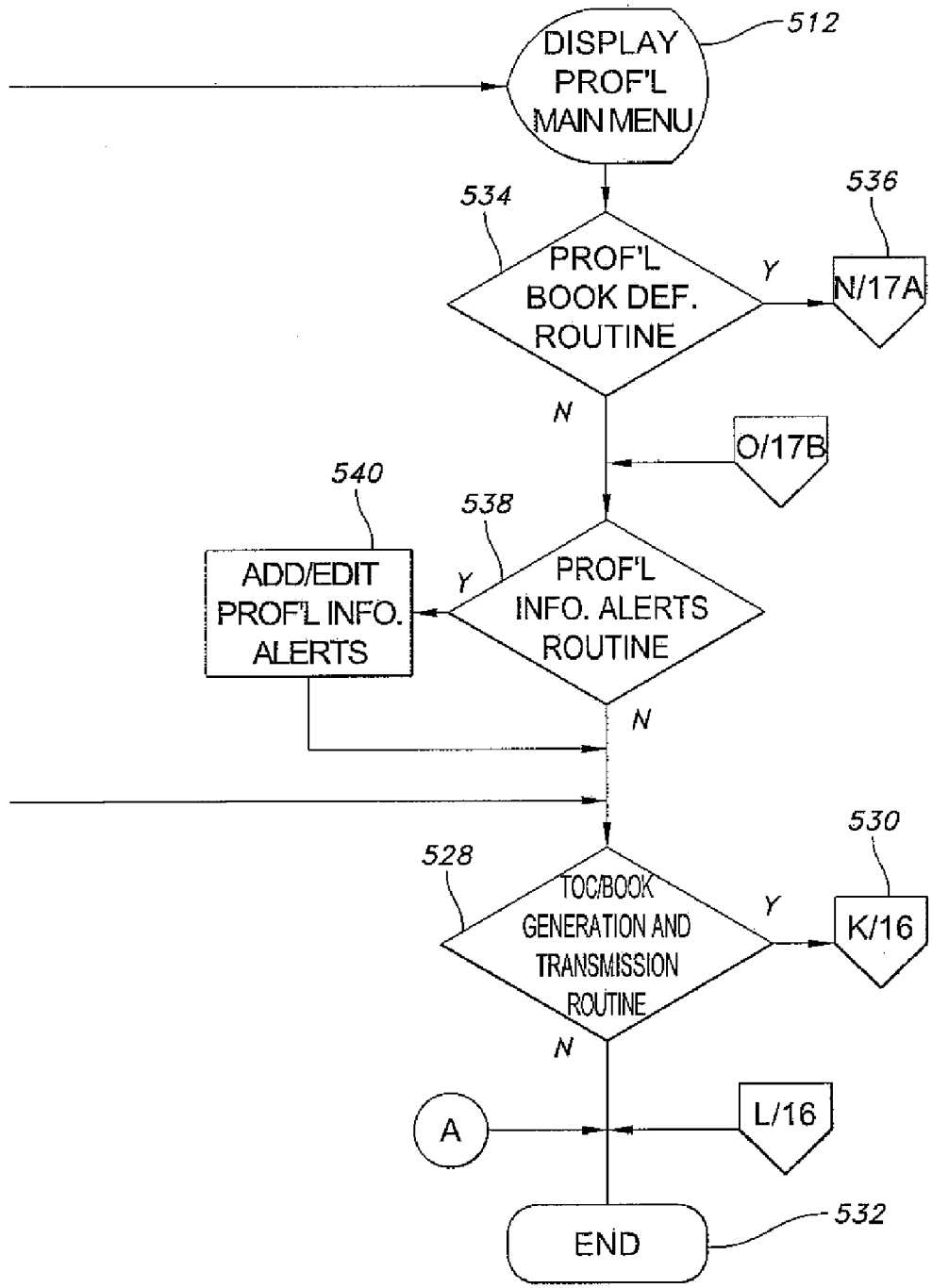

Referring to FIGS. 13A and 13B, a flow chart of a software routine 500 for a main menu used in the second embodiment is illustrated. Main menu routine 500 includes routines for use by consumers and routines for use by professionals in the healthcare industry, e.g., physicians. More specifically, main menu routine 500 provides access to a consumer book definition routine 600 (FIGS. 14A-14CB) at step 520, a consumer information alerts routine at step 524, a TOC/book generation and transmission routine 700 (FIG. 16) at step 528, a professional book definition routine 800 (FIGS. 17A-17C) at step 534, and a professional information alerts routine at step 538. Each routine is discussed more fully herein below.

At step 502, a user accesses the Web site and, at step 504, enters a password for obtaining access to the main menu routine 500. If, at step 506, the password is not accepted, then access to the system is denied at step 508. If the user's password is accepted, then, at step 510, the system determines whether the password is that of a consumer or a professional. If the password is that of a professional, the system proceeds to step 512 and a main menu for a professional is displayed. If the password is that of a consumer, the system proceeds to step 516 and a main menu for a consumer is displayed. Thereafter, the system proceeds to step 520.

At step 520, the system determines whether the consumer selected the consumer book definition routine 600. If the routine was selected, the system proceeds to routine 600 (FIG. 14A) at step 522 (connector I). If, at step 520, the routine was not selected, then the user may proceed to step 524.

At step 524, the system determines whether the consumer selected the consumer information alerts routine. If the routine was selected, the system proceeds to step 526 where a dialog box prompts the consumer to indicate whether he desires to receive information alerts and, if so, the subject matter(s) to which the alerts should pertain. An alert may be activated, for example, when the subject matter is updated in the databases 16 or files 18. Alerts may appear on the consumer's client 26 as scrolling messages or as stationary banners for a fixed period of time. After the consumer selects information alerts, the system proceeds to step 528. If, at step 524, the consumer information alerts routine was not selected, then the user may proceed directly to step 528.

Figure 16:
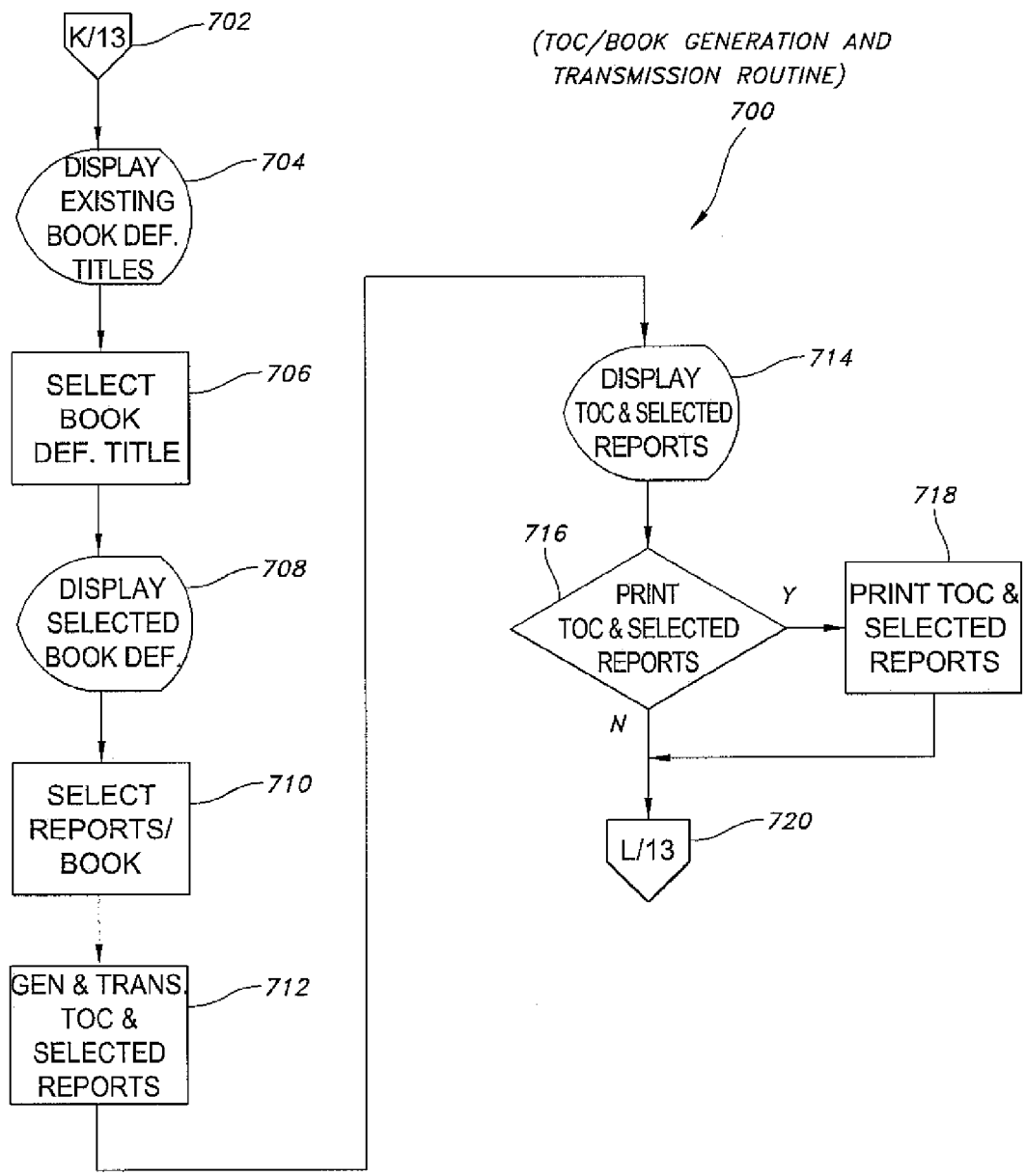
FIG. 16 illustrates a flow chart of a TOC/book generation and transmission routine used in the embodiment of the present invention illustrated in FIG. 12.

At step 528, the system determines whether the consumer selected the TOC/book generation and transmission routine 700 (FIG. 16). If routine 700 was selected, then the system proceeds to routine 700 at step 530 (connector K). If routine 700 was not selected, then the user may proceed directly to step 532 to end the session.

As noted above, if, at step 510, the system determines that the password entered at step 504 is that of a professional, then the system proceeds to step 512 and the main menu for a professional is displayed. Thereafter, the system proceeds to step 534.

Figure 17A:
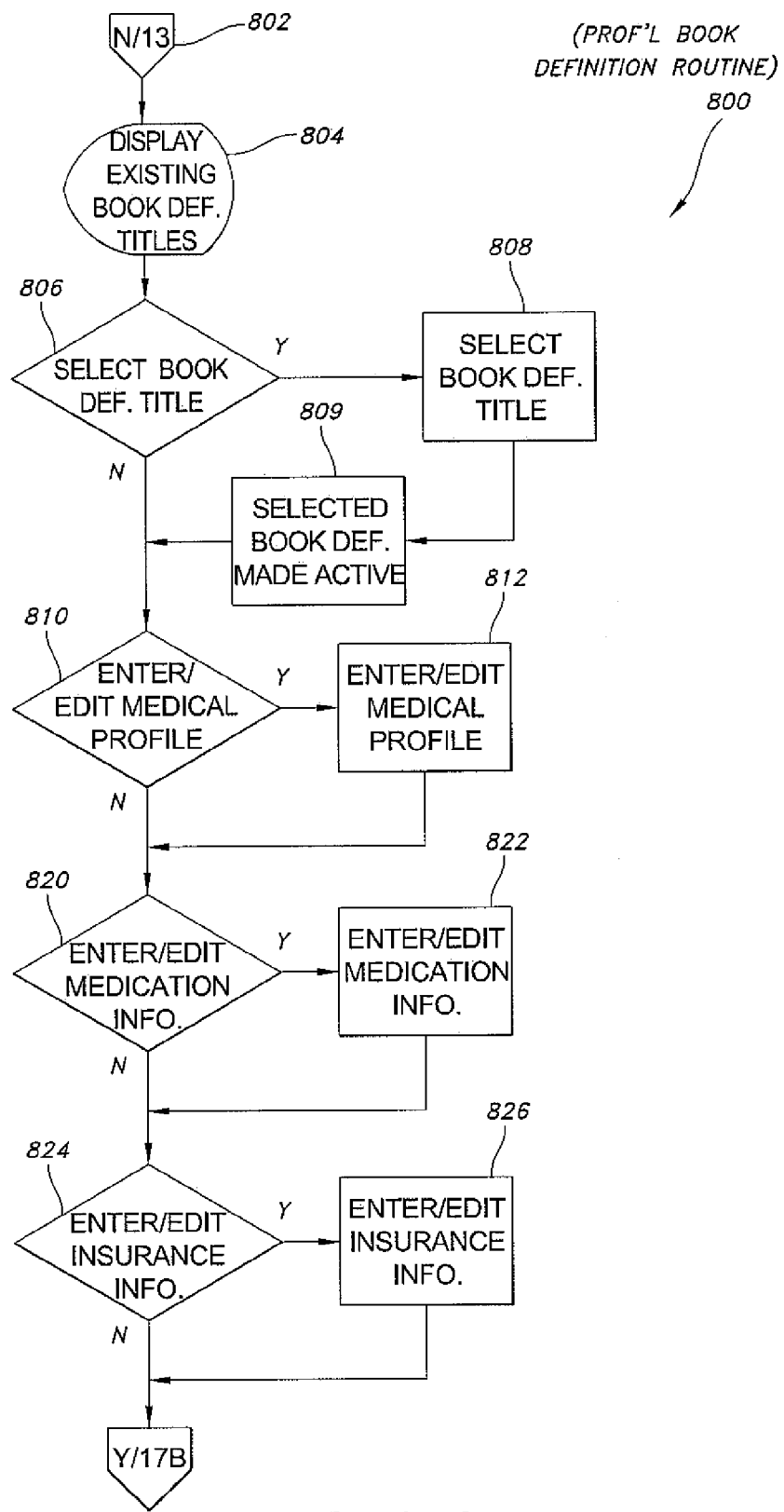
FIGS. 17A-17C illustrate flow charts of a professional book definition routine used in the embodiment of the present invention illustrated in FIG. 12.

At step 534, the system determines whether the professional selected the professional book definition routine 800 (FIG. 17A.) If routine 800 was selected, then the system proceeds to routine 800 at step 536 (connector N). If routine 800 was not selected at step 534, then the system proceeds to step 538.

At step 538, the system determines whether the professional selected the professional information alerts routine. If the routine was selected, then the system proceeds to step 540 where a dialog box prompts the professional to indicate whether he would desire to receive information alerts and, if so, the subject matter(s) to which the alerts should pertain. The professional information alerts routine functions similar to the customer information alerts routine described above with respect to step 526, however, the information is of a nature more appropriate for the professional. For example, alerts may be provided regarding conferences given in new areas of research or alerts may be provided regarding warnings from the Food and Drug Administration. Thereafter, the system proceeds to step 528. If, at step 538, the professional information alerts routine was not selected, then the system proceeds directly to step 528.

At step 528, the system determines whether the professional selected the TOC/book generation and transmission routine 700 (FIG. 16). If routine 700 was selected, then the system proceeds to routine 700 at step 530 (connector K). If routine 700 was not selected, then the system proceeds to step 532 to end the session.

Figure 14A:
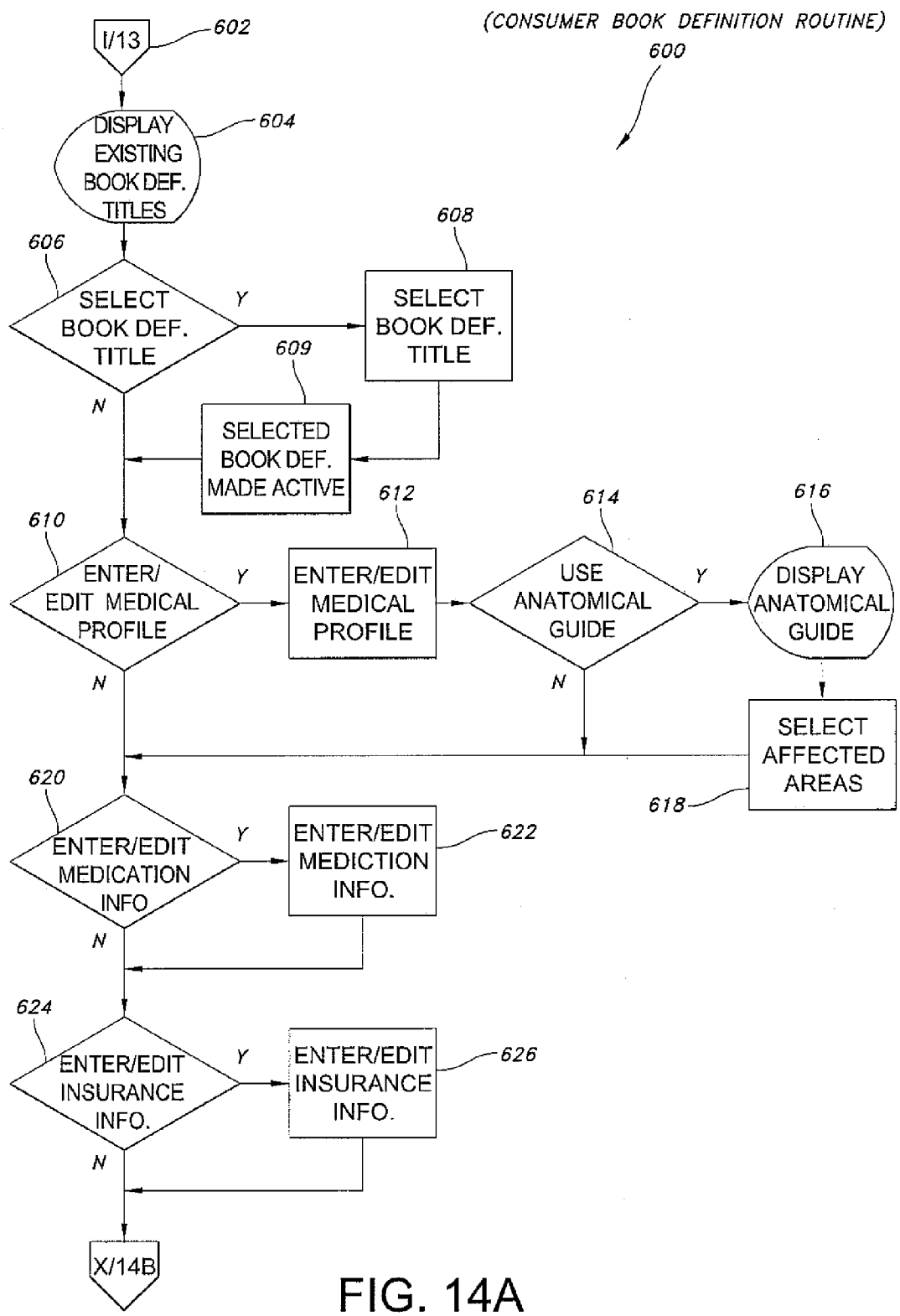
FIGS. 14A-14C illustrate a flow chart of a consumer book definition routine used in the embodiment of the present invention illustrated in FIG. 12.
Figure 14B:
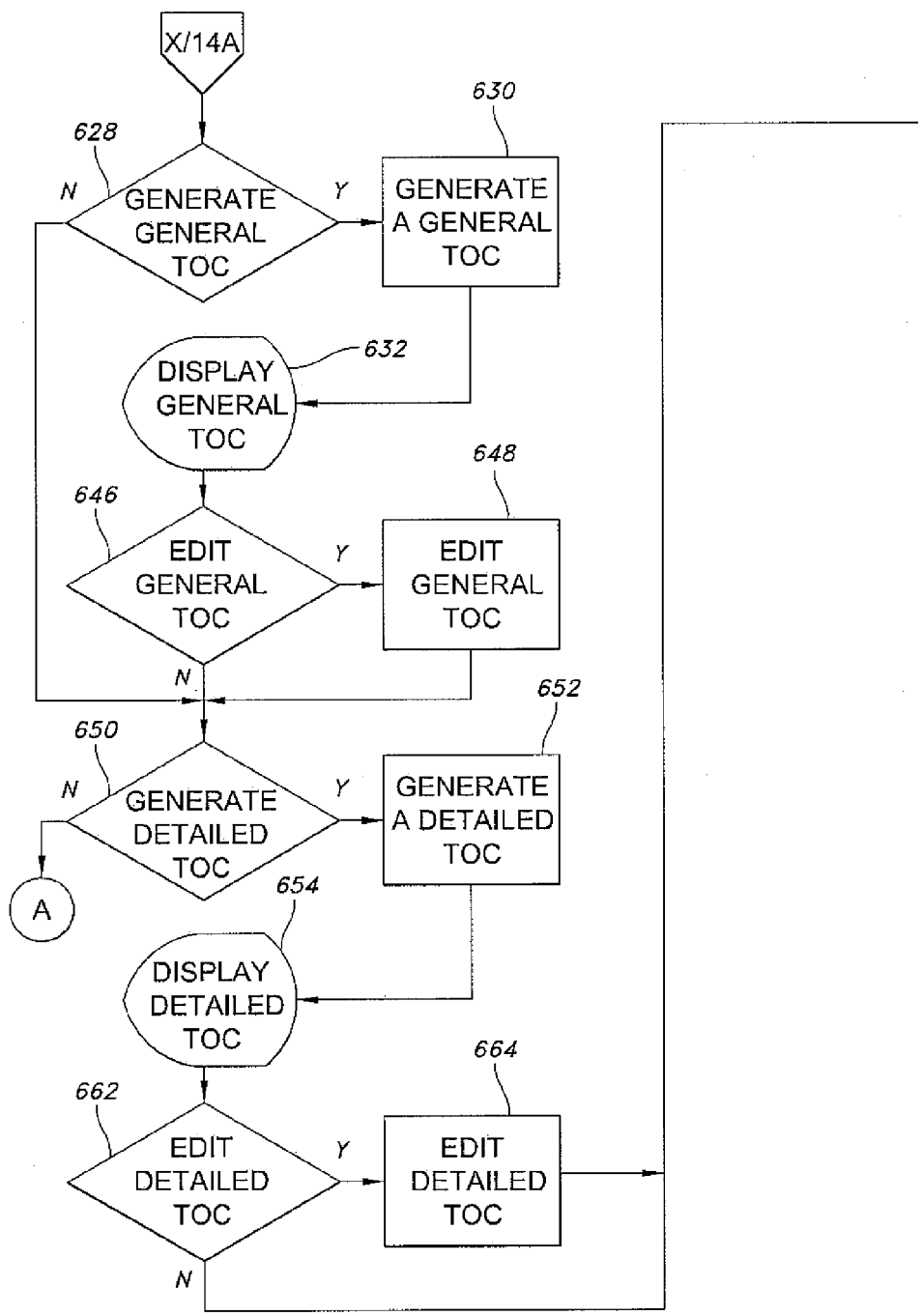
Figure 14C:
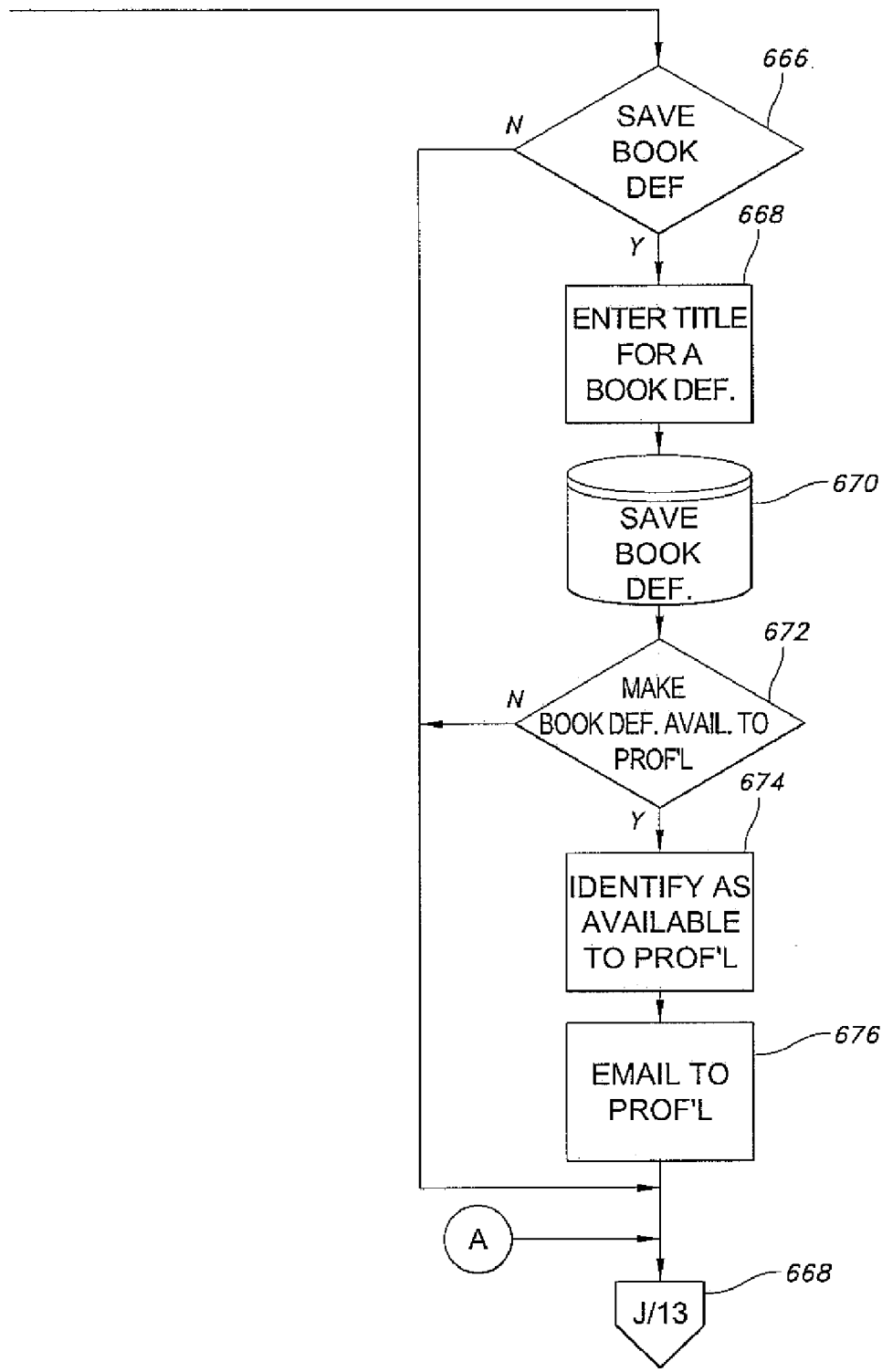

Referring to FIGS. 14A-14C, the consumer book definition routine 600 is illustrated. At step 602 (connector I of FIG. 14A), a consumer enters routine 600 from routine 500 (FIGS. 13A and 13B) and proceeds to step 604. At step 604, a menu is displayed which includes a list of titles of book definitions that were previously created by the consumer or created and made available by a healthcare professional. At step 606, the system determines whether the consumer desires to select a book definition title from the list. If so, then, at step 608, the consumer selects a title from the list. At step 609, the book definition identified by the title is made active. Thereafter, the system proceeds to step 610. A consumer may want to make a book definition active so he can edit and/or print an existing personalized book that is defined by the book definition. If, at step 606, the consumer does not desire to select a book definition title from the list, then the system proceeds directly to step 610 and the consumer can commence creating a new personalized book.

At step 610, the system determines whether the consumer selected to enter/edit medical profile information. If so, then the consumer proceeds to step 612 and enters/edits his medical profile. Thereafter, the system proceeds to step 614. At step 614, the system determines whether the consumer selected to utilize an "anatomical guide" (described below) to facilitate completing the medical profile. If so, the system displays images from the anatomical guide at step 616 and the consumer selects affected areas to assist in completing the medical profile at step 618. Thereafter, the system proceeds to step 620. If, at step 614, the consumer did not select to use the anatomical guide, then the consumer may proceed directly to step 620. If, at step 610, the consumer did not select to enter/edit medical profile information, then the consumer may proceed directly to step 620.

The anatomical guide includes a first-tier image that is made up of multiple sub-images. Each sub-image of the first-tier image is hyper-linked to a different second-tier image. Each second-tier image is also made up of multiple sub-images. Each sub-image of each second-tier image is hyper-linked to a tertiary-tier image. And so forth. The number of images included in the anatomical guide depends on how much detail is to be provided to the consumer. Each sub-image includes descriptive information related to the sub-image. The descriptive information may be, for example, anatomical nomenclature that the consumer may use to more accurately complete his medical profile. The descriptive information may be located proximate each sub-image or separately accessible via a hyper-link.

As an example, the system may display a front and rear image of the human body (a first-tier image). If the consumer has abdominal pain, he will point to the abdominal area in the front image of the human body (a sub-image of the first-tier image) and select it. The system will then retrieve and display an image which shows an enlarged view of the abdomen (a second-tier image). The second-tier image may be, for example, a subcutaneous image for illustrating muscle tissue. If the consumer's pain tends to be in the upper center of his abdomen, then he will point to the upper center area of abdomen (a sub-image of the second-tier image) and select it. The system will then retrieve and display an enlarged image of the upper center region of the abdomen (a tertiary-tier image). And so forth. The tertiary-tier image may be, for example, an image of the upper region of the abdominal cavity for illustrating the esophagus.

At each step, the consumer will consider descriptive information associated with the sub-images or select a hyper-link to retrieve information. The process continues until the consumer obtains sufficient information regarding his abdominal pain so that he can complete his medical profile.

At step 620, the system determines whether the consumer selected to enter/edit medication information. If so, then the consumer enters/edits his medication information at step 622. Such information may include the brand name and delivery regiment of each drug that the consumer is presently taking, herbs the consumer is presently using, etc. Thereafter, the system proceeds to step 624. If, at step 620, the consumer did not select to enter/edit medication information, then the consumer may proceed directly to step 624.

At step 624, the system determines whether the consumer selected to enter/edit insurance information. If so, then the consumer enters/edits his insurance information at step 626. Thereafter, the system proceeds to step 628 (FIGS. 14B and 14C) via connector X. If, at step 624, the consumer did not select to enter/edit insurance information, then he may proceed directly to step 628.

Referring to FIGS. 14B and 14C, at step 628, the system determines whether the consumer selected to receive a general table of contents based on the descriptive information. If so, then, at step 630, the system generates a general table of contents and proceeds to step 632. At step 632, the general table of contents is transmitted to the consumer and displayed on the consumer's client 26.

Referring to FIG. 15A, a Web page 634 that may be displayed at step 632 is illustrated. The Web page 634 includes a level of detail control bar 636, an options control bar 640, and a general table of contents 642. The general table of contents 642 includes headings representing categories of information available to the consumer. The categories of information that are included in the general table of contents are dependant upon the information entered by the consumer at steps 612, 618, 622, and 626 (FIG. 14A). If the consumer entered the symptoms of an illness at step 612, then the general table of contents will include, for example, the categories "Diagnosis," "Synonyms," "Incidents," and other related categories. It is intended that the databases 16 and files 18 are sufficiently comprehensive so that a wide variety of categories are available to the consumer. For example, entering the symptoms of an illness may result in a general table of contents including the category "care facilities" because the databases 16 include information on care facilities that specialize in treating the particular illness.

Next to each category in a general table of contents is a check-off box. The check-off boxes allow a consumer to select the categories of information that he desires to include in a personalized book. In the case where a consumer is editing a book definition, the general table of contents may already include checked-off categories.

The level of detail control bar 636 enables a consumer to quickly select/deselect categories of information. Included are "1st" through "5th" level controls, a "Select All" control, and a "Deselect All" control. For example, selecting the 1st-level control will automatically select level 1 categories of information in the general table of contents (e.g., "Diagnosis" through "Prognosis".) Selecting the 2nd-level control will automatically select level 2 categories of information in the general table of contents (e.g., "Practitioners" through "Home Care".) Selecting the 3rd-level control will automatically select level 3 categories of information in the general table of contents (e.g., "Articles Relating to the Diagnosis and Prognosis" through "Thought Leader Center Ratings".) Selecting the 4th-level control will automatically select level 4 categories of information in the general table of contents (e.g., "Clinical Studies" through "Video Clips".) And selecting the 5th-level control will automatically select level 5 categories of information in the general table of contents (e.g., "Conferences" through "Association Ratings".) The 5th-level control is only available to professionals.

The options bar 640 includes controls for a consumer to select categories of information concerning traditional medicine and/or non-traditional medicine. The options bar also includes a selection for indicating that questions should be included for a consumer to ask his professional healthcare provider, e.g., his physician. Web page 634 also includes a "Transmit Selections" button 644, for transmitting the above described selections to the server 12.

At step 646, the system determines whether the consumer selected to edit the general table of contents. If so, then the consumer edits the general table of contents at step 648 in the manner described above (e.g., by selecting/deselecting categories, levels of details, and options) and transmits the selections to the server 12 using the "Transmit Selections" button 644. Thereafter, the system proceeds to step 650. If, at step 646, the consumer did not select to edit the general table of contents (thereby, for example, retaining earlier category heading selections in an active book definition), then the consumer may proceed directly to step 650. If, at step 628, the consumer did not select to receive a general table of contents, then the consumer may proceed directly to the main menu routine 500 at step 668 (connector J).

At step 650, the system determines whether the consumer selected to receive a detailed table of contents. If so, then, at step 652, the system generates a detailed table of contents and proceeds to step 654. At step 654, the detailed table of contents is transmitted to the consumer and displayed to the consumer's client 26. The detailed table of contents includes category headings that match the headings of categories selected by the consumer in step 648. Under the category headings are titles of related reports which are available, for example, in the databases 16, files 18, and/or other sites 24.

Referring to FIG. 15B, a Web page 656 that may be displayed to the consumer is illustrated and includes a detailed table of contents 658. For this example, it is assumed that a consumer selected the category headings "Diagnosis," "Tests/Screens for Diagnosis," and "Medical Centers" (that are "Local" to Stamford, CT) from the general table of contents 642 (FIG. 15A). In such case, the detailed table of contents 658 includes headings that match the selected category headings and various related reports under each heading.

More specifically, the detailed table of contents 658 includes under the category heading "Diagnosis" a "Coronary Disease Report;" under the category heading "Tests/Screens for Diagnosis" an "Electrocardiagram Report," "Stress Test Report," "Nuclear Scanning Report," and a "Coronary Angiography Report;" under the category heading "Medical Centers" ("Local" to Stamford, CT) a "Greenwich Hospital Capabilities Report," "Stamford Hospital Capabilities Report," and a "Norwalk Hospital Capabilities Report."

Next to each report in the detailed table of contents 658 is a check-off box. The check-off boxes allow a consumer to select the reports that he desires to include as part of a book definition. In the case where a consumer is editing a book definition, the detailed table of contents will already include checked off reports. Web page 656 also includes a "Transmit Selections" button 660, for transmitting the above-described selections to the server 12.

The reports that are included in the detailed table of contents depends upon the information entered by the consumer at steps 612, 618, 622, and 626 (FIG. 14A). For example, in detailed table of contents 658 (FIG. 15B) the "Coronary Disease Report" under the "Diagnosis" category heading may have resulted because a consumer entered information at step 612 (FIG. 14A) indicating that he had chest pains (angina), shortness of breath, or a burning or squeezing sensation behind his breast bone.

As an example of the versatility of the present embodiment, assume that a consumer entered a query which included a symptom at step 612 and insurance information at step 626 resulting in a report that describes a particular medical condition the consumer may have and a report concerning drugs that may be used to treat the medical condition. The drug report may include not only those drugs that are covered in whole or in part by the consumer's insurance policy, i.e., those on the insurance company's formulary, but also the drugs that are not covered. Furthermore, the list may include for comparison purposes the co-pays for each covered drug, side effects, typical delivery regiments, interactions, local pharmacies that carry each drug, etc.

Referring to FIGS. 14B and 14C, at step 662, the system determines whether the consumer selected to edit the detailed table of contents. If so, then the consumer edits the detailed table of contents at step 664 in the manner described above (e.g., by selecting/deselecting reports.) Thereafter, the system proceeds to step 666. If, at step 662, the consumer did not select to edit the detailed table of contents, then he may proceed directly to step 666. If, at step 650, the consumer did not select to generate a detailed table of contents, then he may proceed directly to the main menu routine 500 at step 668 (connector J).

Those of ordinary skill in the art will appreciate that the table of contents now defines the contents of a book that has been customized by the consumer. It should be readily apparent that this aspect of the second embodiment provides a significant advantage to consumers in that they are able to quickly obtain reports that concern their specific needs. Furthermore, the embodiment makes it unnecessary for consumers to sift through a large number of irrelevant reports.

At step 666, the system determines whether the consumer selected to save the book definition. If the book definition is new, the consumer enters a title for the book definition at step 668 and it is stored at step 670. If the book definition is not new (i.e., it's an edited version), the book definition will already have a title and the consumer may either store the book definition under the old title or rename the book definition at step 670. Thereafter, at step 672, the system determines whether the consumer selected to make the book definition available to a healthcare professional (e.g., a physician). If so, then, at step 674, the consumer identifies the healthcare professional and the system identifies the book definition as available to the healthcare professional. At step 676, the system automatically e-mails the healthcare professional that the consumer's book definition is available. Thereafter, the consumer returns to the main menu routine 500 at step 668 (connector J). If, at step 672, the consumer did not select to make the book available to a healthcare professional, then the consumer returns directly to the main menu routine 500 at step 668 (connector J). If, at step 666, the consumer did not select to save the book definition, then the consumer returns directly to the main menu routine 500 at step 668 (connector J).

Referring to FIG. 16, a flow chart illustrates the TOC/book generation and transmission routine 700. At step 702 (connector K), a consumer enters routine 700 from the main menu routine 500 and proceeds to step 704. At step 704, a menu is displayed which includes a list of titles of book definitions previously created and presently available to the consumer. At step 706, the consumer selects a title and, at step 708, the book definition (which includes a list of category headings and titles of reports) is displayed on the consumer's client 26. At step 710, the consumer selects one or more of the reports from the book definition for generation and delivery to his client 26. For example, a consumer may desire to initially receive an article that describes a particular medical condition in a general manner so that he may become better acquainted with the subject matter before he has the entire book transmitted to his client 26. Thereafter, the system proceeds to step 712.

At step 712, the system generates and transmits to the consumer's client 26 a table of contents listing the category headings and titles of reports from the book definition that was selected at step 706, and the reports that were selected at step 710. Of course, if the consumer selected the entire book of reports at step 710, then all of the reports from the personalized book will be generated and transmitted to the consumer's client 26 at step 712. At step 714, the table of contents and the titles of the selected reports are displayed on the consumer's client 26. Thereafter, the system proceeds to step 716.

At step 716, the client 26 determines whether the consumer selected to print the table of the contents for the consumer's personalized book and one or more of the selected reports. If so, then, at step 718, the client 26 prints the table of contents and the one or more selected reports. Thereafter, the consumer may return to the main menu routine 500 at step 720 (connector L). If, at step 716, the consumer did not select to print the table of contents for his personalized book and the one or more of the selected reports, then the consumer may proceed directly to the main menu routine 500 at step 720 (connector L).

Figure 17B:
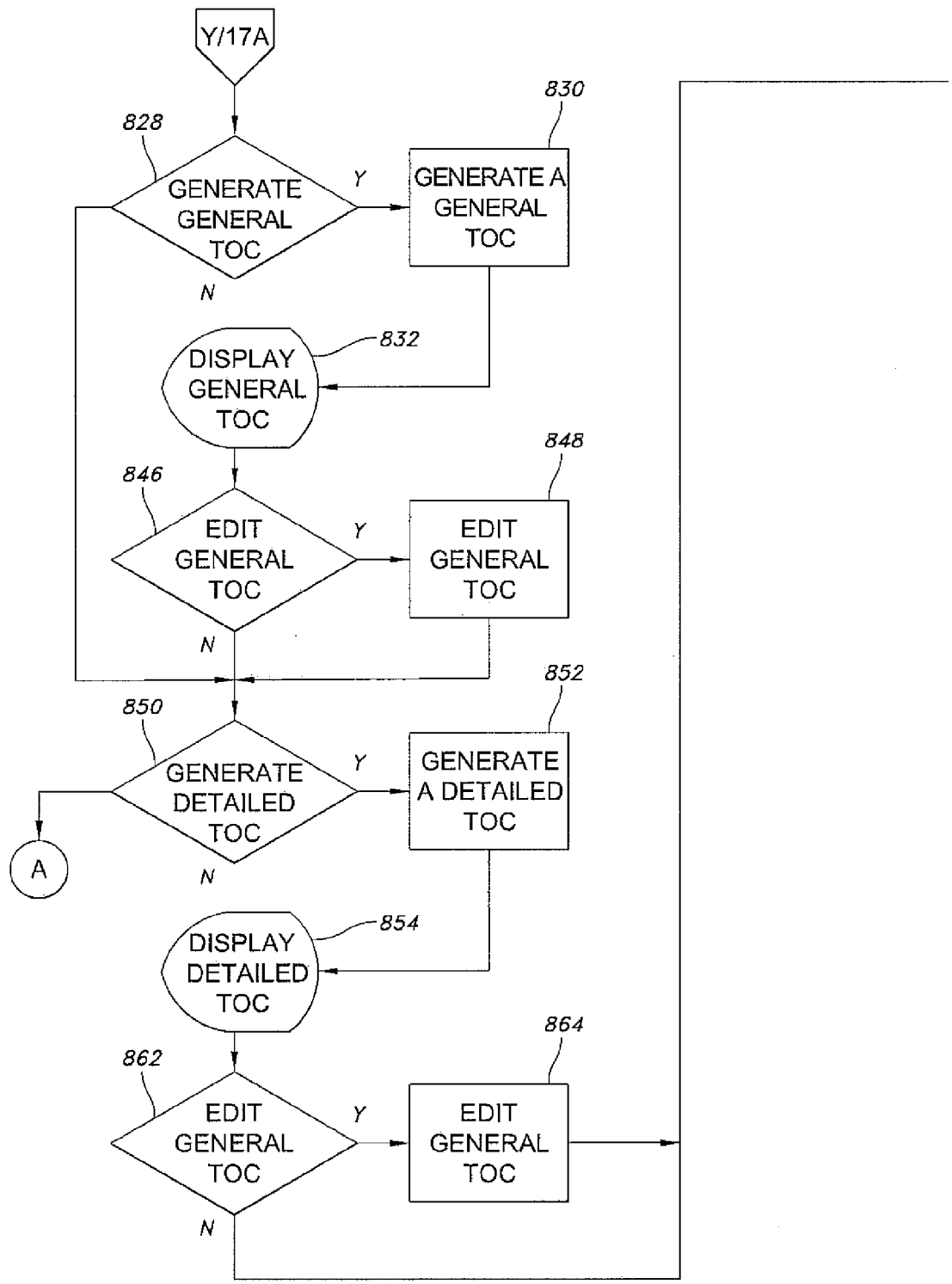
Figure 17C:
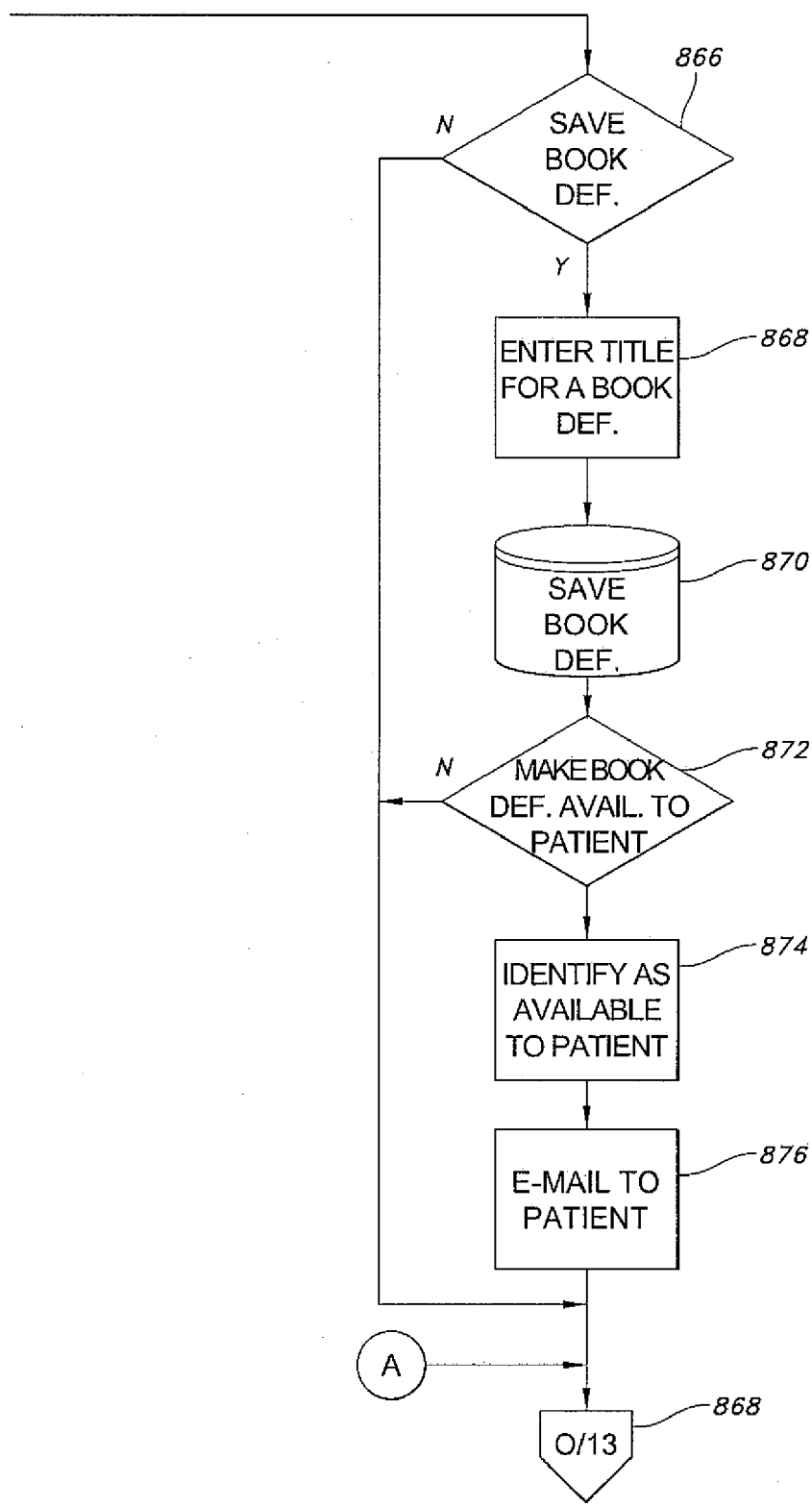

Referring to FIGS. 17A-17C, the professional book definition routine 800 is illustrated. At step 802 (connector N of FIG. 17A), a healthcare professional enters routine 800 from routine 500 (FIGS. 13A and 13B) and proceeds to step 804. At step 804, a menu is displayed which includes a list of titles of book definitions that were previously created by the professional or created and made available by, for example, one of the professional's patients. At step 806, the system determines whether the professional desires to select a book definition title from the list. If so, then, at step 808, the professional selects a title from the list. At step 809, the book definition identified by the title is made active. Thereafter, the system proceeds to step 810. A professional may want to make a book definition active so he can edit and/or print an existing personalized book that is defined by the book definition. If, at step 806, the professional does not desire to select a book definition title from the list, then the system proceeds directly to step 810 and the professional can commence creating a new personalized book.

At step 810, the system determines whether the professional selected to enter/edit medical profile information of a patient. If so, then the professional proceeds to step 812 and enters/edits the medical profile. Thereafter, the system proceeds to step 820. If, at step 810, the professional did not select to enter/edit a medical profile, then the professional may proceed directly to step 820.

At step 820, the system determines whether the professional selected to enter/edit the patient's medication information. If so, then the professional enters/edits the medication information at step 822. Such information may include the brand name and delivery regiment of each drug that the patient is presently taking, herbs the patient is presently using, etc. Thereafter, the system proceeds to step 824. If, at step 820, the professional did not select to enter/edit medication information, then the professional may proceed directly to step 824.

At step 824, the system determines whether the professional selected to enter/edit the patient's insurance information. If so, then the professional enters/edits the insurance information at step 826. Thereafter, the system proceeds to step 828 (FIGS. 17B and 17C) via connector Y. If, at step 824, the professional did not select to enter/edit insurance information, then he may proceed directly to step 828.

Referring to FIGS. 17B and 17C, at step 828, the system determines whether the professional selected to receive a general table of contents based on the descriptive information. If so, then, at step 830, the system generates a general table of contents and proceeds to step 832. At step 832, the general table of contents is transmitted to the professional and displayed on the professional's client 26. The general table of contents is similar to the general table of contents described herein above and exemplified in FIG. 15A.

At step 846, the system determines whether the professional selected to edit the general table of contents. If so, then the professional edits the general table of contents at step 848 in the manner described above (e.g., by selecting/deselecting categories, levels of details, and options) and transmits the selections to the server 12 using the "Transmit Selections" button 644. Thereafter, the system proceeds to step 850. If, at step 846, the professional did not select to edit the general table of contents, then the professional may proceed directly to step 850. If, at step 828, the professional did not select to receive a general table of contents, then he may proceed directly to the main menu routine 500 at step 868 (connector O).

At step 850, the system determines whether the professional selected to receive a detailed table of contents. If so, then, at step 852, the system generates a detailed table of contents and proceeds to step 854. At step 854, the detailed table of contents is transmitted to the professional and displayed on the professional's client 26. The detailed table of contents is similar to the detailed table of contents described herein above and exemplified in FIG. 15B.

At step 862, the system determines whether the professional selected to edit the detailed table of contents. If so, then the professional edits the detailed table of contents at step 864 in the manner described above (e.g., by selecting/deselecting reports.) Thereafter, the system proceeds to step 866. If, at step 862, the professional did not select to edit the detailed table of contents, then he may proceed directly to step 866. If, at step 850, the professional did not select to generate a detailed table of contents, then he may proceed directly to the main menu routine 500 at step 868 (connector O).

Those of ordinary skill in the art will appreciate that the book definition now defines a book of reports that has been customized by the professional to suit his particular needs. It should be readily apparent that this aspect of the second embodiment provides a significant advantage to physicians in that it permits them, for example, to conduct research to learn more about a patient's condition or to provide a patient a personalized book of information concerning his medical condition.

At step 866, the system determines whether the professional selected to save the book definition. If the book definition is new, the professional enters a title for the book definition at step 868 and it is stored at step 870. If the book definition is not new (i.e., it is an edited version), the book definition will already have a title and the professional may either store the book definition under the old title or rename the book definition at step 870. Thereafter, at step 872, the system determines whether the professional selected to make the book definition available to a patient. If so, then, at step 874, the professional identifies the patient and the system identifies the book definition as available to the patient.

An alternate method by which the system may allow a professional to make a book definition available to a patient is by storing the book definition in the storage device 14 so that it is accessible only by utilizing a particular code. In such case, the professional will inform the patient of the access code. The patient may then access the book definition utilizing the code and download any or all of the reports to his client 26.

At step 876, the system automatically e-mails the patient that the healthcare professional's book definition is available. Thereafter, the professional returns to the main menu routine 500 at step 868 (connector O). If, at step 872, the professional did not select to make the book available to the patient, then the professional returns directly to the main menu routine 500 at step 868 (connector O). If, at step 866, the professional did not select to save the book definition, then the professional returns directly to the main menu routine 500 at step 868 (connector O).

Referring to FIG. 16, the flow chart illustrates the TOC/book generation and transmission routine 700. At step 702 (connector K), a professional enters routine 700 from the main menu routine 500 and proceeds to step 704. At step 704, a menu is displayed which includes a list of titles of book definitions previously created and presently available to the professional. At step 706, the professional selects one or more of the reports from a title and, at step 708, the book definition (which includes a list of category headings and titles or reports) is displayed on the professional's client 26. At step 710, the professional selects one or more of reports from the book definition for generation and delivery to his client 26. Thereafter, the system proceeds to step 712.

At step 712, the system generates and transmits to the professional's client 26 a table of contents listing the category headings and titles of reports from the book definition that was selected at step 706 and the reports that were selected at step 710. Of course, if the professional selected the entire book of reports at step 710, then all of the reports from the personalized book will be generated and transmitted to the professional's client 26 at step 712. At step 714, the table of contents and the titles of the selected reports are displayed on the professional's client 26. Thereafter, the system proceeds to step 716.

At step 716, the client 26 determines whether the professional selected to print the table of contents for the professional's personalized book and one or more of the selected reports. If so, then, at step 718, the client prints the table of contents and the one or more selected reports. Thereafter, the professional may return to the main menu routine 500 at step 720 (connector L). If, at step 716, the professional did not select to print the table of contents for his personalized book and the one or more of the selected reports, then the professional may proceed directly to the main menu routine 500 at step 720 (connector L).

It should be clear from the foregoing disclosure that the present system and method for creating and transmitting a book of reports over a computer network will effectively assist consumers and professionals to focus their searches for information over the Internet. In addition, the system and method will allow consumers and professionals to quickly review and organize their search results. Furthermore, the system and method is easy to operate and readily integrates into the various technical systems and methods presently employed by consumers and professionals.

Those of ordinary skill in the art should readily appreciate that industries other than the pharmaceutical and healthcare industries can benefit from the various embodiments of the present invention. It is envisioned, for example, that systems may be made to enable an engineer to research and prepare a personalized book concerning a particular technical subject matter, to enable a historian to research and prepare a personalized book concerning a particular historical event, or to enable a consumer to research and prepare a personalized book concerning how to repair his car.

While the system and method disclosed herein above has been described with respect to various specific embodiments, those of ordinary skill in the art will readily appreciate that various modifications, changes, and enhancements may be made thereto without departing from the spirit and scope of the invention as defined by the appended claims.

What is claimed is:

1. A method for creating and transmitting a book of reports over a computer network, comprising:
   storing at least two report definitions in a storage device of a server;
   creating a book with which the at least two report definitions are to be associated;
   associating the at least two report definitions with the book;
   receiving a request for the book from a user;
   generating a first report for a first of the at least two report definitions associated with the book based on network-based searching of a plurality of databases, wherein at least one contribution to said first report is derived from a first database among said plurality of databases and at least one additional contribution to said first report is derived from a second database among said plurality of databases that is distinct from said first database, yielding a first report that includes multiple contributions originating from distinct databases;
   generating a second report for a second of the at least two report definitions associated with the book based on network-based searching of a plurality of databases, wherein at least one contribution to said second report is derived from a third database among said plurality of databases and at least one additional contribution to said second report is derived from a fourth database among said plurality of databases that is distinct from said third database, yielding a second report that includes multiple contributions originating from distinct databases; and
   transmitting the book of reports that include the first and second reports to the user.

2. The method as recited in claim 1, further comprising the step of receiving the at least two report definitions from the user, wherein the report definitions were created with at least one routine.

3. The method as recited in claim 2, wherein a report definition created by the report definition routine produces a chart when processed by the server.

4. The method as recited in claim 2, wherein the product query routine includes at least one related routine.

5. The method as recited in claim 4, wherein said at least one related routine is a diagnosis filter routine.

6. The method as recited in claim 4, wherein said at least one related routine is an MOA filter routine.

7. The method as recited in claim 4, wherein said at least one related routine is a marketer filter routine.

8. The method as recited in claim 4, wherein said at least one related routine is a lifecycle filter routine.

9. The method as recited in claim 4, wherein said at least one related routine is a status filter routine.

10. The method as recited in claim 4, wherein said at least one related routine is a countries routine.

11. The method as recited in claim 2, wherein a report definition created by the product query routine produces a product specification when processed by the server.

12. The method as recited in claim 2, wherein said at least one routine is a report definition routine.

13. The method as recited in claim 12, wherein the report definition routine includes at least one additional routine.

14. The method as recited in claim 13, wherein said at least one additional routine is a filters routine.

15. The method as recited in claim 13, wherein said at least one additional routine is a columns routine.

16. The method as recited in claim 13, wherein said at least one additional routine is a countries routine.

17. The method as recited in claim 13, wherein said at least one additional routine is an options routine.

18. The method as recited in claim 14, wherein the filters routine includes at least one associated routine.

19. The method as recited in claim 18, wherein said at least one associated routine is a diagnosis filter routine.

20. The method as recited in claim 18, wherein said at least one associated routine is an MOA filter routine.

21. The method as recited in claim 18, wherein said at least one associated routine is a marketer filter routine.

22. The method as recited in claim 18, wherein said at least one associated routine is a lifecycle filter routine.

23. The method as recited in claim 18, wherein said at least one associated routine is a status filter routine.

24. The method as recited in claim 2, wherein said at least one routine is a product query routine.

25. The method as recited in claim 1, further comprising the steps of generating a table of contents for the book including titles of the reports and transmitting the table of contents to the user.

26. The method as recited in claim 1, further comprising the step of formatting descriptive headings in each of the reports prior to transmitting the book of reports to the user, the descriptive headings being useful for generating a table of contents by a client.

27. The method as recited in claim 1, wherein the reports are selected from the group consisting of documents, articles, abstracts, product specifications, charts, still images, video clips, and audio clips.

28. A computer system for creating and transmitting a book of reports over a computer network, comprising:
a processor in communication with a storage device, wherein the processor is operative to
store at least two report definitions in the storage device;
create a book with which the at least two report definitions are to be associated;
associate the at least two report definitions with the book;
receive a request for the book from a user;
perform network-based searching of a plurality of databases based on said at least two report definitions;
generate a first report for a first of the at least two report definitions associated with the book based on said network-based searching, wherein at least one contribution to said first report is derived from a first database among said plurality of databases and at least one additional contribution to said first report is derived from a second database among said plurality of databases that is distinct from said first database, yielding a first report that includes multiple contributions originating from distinct databases;
generate a second report for a second-of the at least two report definitions associated with the book based on said network-based searching, wherein at least one contribution to said second report is derived from a third database among said plurality of databases and at least one additional contribution to said second report is derived from a fourth database among said plurality of databases that is distinct from said third database, yielding a second report that includes multiple contributions originating from distinct databases; and
transmit the book of reports to the user.

29. The computer system as recited in claim 28, wherein the processor is further operative to receive the at least two report definitions from the user, wherein the report definitions were created with a routine.

30. The computer system as recited in claim 29, wherein a report definition created by the report definition routine produces a chart when processed by the server.

31. The computer system as recited in claim 29, wherein said routine is a report definition routine.

32. The computer system as recited in claim 31, wherein the report definition routine includes at least one associated routine.

33. The computer system as recited in claim 32, wherein said at least one associated routine is a filters routine.

34. A computer system as recited in claim 32, wherein said at least one associated routine is a columns routine.

35. The computer system as recited in claim 32, wherein said at least one associated routine is a countries routine.

36. The computer system as recited in claim 32, wherein said at least one associated routine is an options routine.

37. The computer system as recited in claim 33, wherein the filters routine includes at least one related routine.

38. The computer system as recited in claim 37, wherein said at least one related routine is a diagnosis filter routine.

39. The computer system as recited in claim 37, wherein said at least one related routine is an MOA filter routine.

40. The computer system as recited in claim 37, wherein said at least one related routine is a marketer filter routine.

41. The computer system as recited in claim 37, wherein said at least one related routine is a lifecycle filter routine.

42. The computer system as recited in claim 37, wherein said at least one related routine is a status filter routine.

43. The computer system as recited in claim 29, wherein said routine is a product query routine.

44. The computer system as recited in claim 43, wherein the product query routine includes at least one related routine.

45. The computer system as recited in claim 44, wherein said at least one related routine is a diagnosis filter routine.

46. The computer system as recited in claim 44, wherein said at least one related routine is an MOA filter routine.

47. The computer system as recited in claim 44, wherein said at least one related routine is a marketer filter routine.

48. The computer system as recited in claim 44, wherein said at least one related routine is a lifecycle filter routine.

49. The computer system as recited in claim 44, wherein said at least one related routine is a status filter routine.

50. The computer system as recited in claim 43, wherein a report definition created by the product query routine produces a product specification when processed by the server.

51. The computer system as recited in claim 28, wherein the processor is further operative to generate a table of contents for the book including titles of the reports and transmitting the table of contents to the user.

52. The computer system as recited in claim 28, wherein the processor is further operative to format descriptive headings in each of the reports prior to transmitting the book of reports to the user, the descriptive headings being useful for generating a table of contents by a client.

53. The computer system as recited in claim 28, wherein the reports are selected from the group consisting of documents, articles, abstracts, product specifications, charts, still images, video clips, and audio clips.

* * * * *